the present invention relates to an immunogenic composition comprising an antigenic peptide of formula (I) below: Nt-S-X1-X2-X3-K-X4-Ct (I) [SEQ ID No 1], wherein Nt consists of a peptide having from 0 to 50 amino acids in length, Ct consists of a peptide having from 0 to 50 amino acids in length, each of X1 to X4 consists of an amino acid residue, wherein: (i) X1 means the specific amino acid W or (ii) X1 means any amino acid residue excepted W, (i) X2 means the specific amino acid S or (ii) X2 means any amino acid residue excepted S, (i) X3 means the specific amino acid N or (ii) X3 means any amino acid residue excepted N, (i) X4 means the specific amino acid S or (ii) X4 means any amino acid residue excepted S, with the proviso that three out of the four amino acid residues X1, X2, X3 and X4 mean the specific amino acid defined in their respective meaning (i) above, and the remaining amino acid residue among X1 to X4 means any amino acid residue excepted the specific amino acid residue defined in its meaning (i), for preventing and/or treating an infection of an individual with an HIV-1 virus.

(12) United States Patent
Debre et al.

(10) Patent No.: US 10,174,080 B2
(45) Date of Patent: Jan. 8, 2019

(54) COMPOSITIONS FOR PREVENTING AND/OR TREATING AN INFECTION BY AN HIV-1 VIRUS

(71) Applicants: Patrice Debre, Paris (FR); Vincent Vieillard, Paris (FR)

(72) Inventors: Patrice Debre, Paris (FR); Vincent Vieillard, Paris (FR)

(73) Assignees: INSERM (Institut National de la Sante et de la Recherche Medicale), Paris (FR); INNAVIRVAX, Evry (FR)

( * ) Notice: Subject to any disclaimer, the term of this patent is extended or adjusted under 35 U.S.C. 154(b) by 0 days.

(21) Appl. No.: 15/712,195

(22) Filed: Sep. 22, 2017

(65) Prior Publication Data

US 2018/0057535 A1    Mar. 1, 2018

Related U.S. Application Data

(63) Continuation of application No. 14/870,287, filed on Sep. 30, 2015, now Pat. No. 9,802,983, which is a continuation of application No. 14/111,790, filed as application No. PCT/IB2012/051842 on Apr. 13, 2012, now Pat. No. 9,181,299.

(30) Foreign Application Priority Data

Apr. 15, 2011 (EP) .................................. 11305451

(51) Int. Cl.
| | | |
|---|---|---|
| *A61K 39/00* | (2006.01) |
| *C12Q 1/68* | (2018.01) |
| *C07K 14/00* | (2006.01) |
| *A61K 39/395* | (2006.01) |
| *C07H 21/04* | (2006.01) |
| *C07K 7/08* | (2006.01) |
| *C07K 16/10* | (2006.01) |
| *C07K 14/005* | (2006.01) |
| *A61K 39/12* | (2006.01) |
| *A61K 45/06* | (2006.01) |
| *G01N 33/569* | (2006.01) |

(52) U.S. Cl.
CPC ................ *C07K 7/08* (2013.01); *A61K 39/12* (2013.01); *A61K 45/06* (2013.01); *C07K 14/005* (2013.01); *C07K 16/1063* (2013.01); *G01N 33/56988* (2013.01); *A61K 39/00* (2013.01); *A61K 2039/55566* (2013.01); *A61K 2039/6081* (2013.01); *C07K 2317/21* (2013.01); *C07K 2317/34* (2013.01); *C07K 2317/76* (2013.01); *C12N 2740/16122* (2013.01); *C12N 2740/16134* (2013.01); *G01N 2333/16* (2013.01); *G01N 2469/20* (2013.01)

(58) Field of Classification Search
None
See application file for complete search history.

*Primary Examiner* — Barry A Chestnut
(74) *Attorney, Agent, or Firm* — W&C IP

(57) ABSTRACT

14 Claims, 21 Drawing Sheets
Specification includes a Sequence Listing.

```
Wild-type  :  NH2-C-P-W-N-A-S-W-S-N-K-S-L-D-D-I-W-COOH
S613A (M1) :  NH2-C-P-W-N-A-A-W-S-N-K-S-L-D-D-I-W-COOH
W614A (M2) :  NH2-C-P-W-N-A-S-A-S-N-K-S-L-D-D-I-W-COOH
S615A (M3) :  NH2-C-P-W-N-A-S-W-A-N-K-S-L-D-D-I-W-COOH
N616A (M4) :  NH2-C-P-W-N-A-S-W-S-A-K-S-L-D-D-I-W-COOH
K617A (M5) :  NH2-C-P-W-N-A-S-W-S-N-A-S-L-D-D-I-W-COOH
S618A (M6) :  NH2-C-P-W-N-A-S-W-S-N-K-A-L-D-D-I-W-COOH
```

Figure 1

COMPOSITIONS FOR PREVENTING AND/OR TREATING AN INFECTION BY AN HIV-1 VIRUS

CROSS-REFERENCE TO RELATED APPLICATIONS

This application is a continuation of U.S. Ser. No. 14/870,287 filed Sep. 30, 2015, now U.S. Pat. No. 9,802,983, which itself was a continuation of U.S. Ser. No. 14/111,790 filed Oct. 15, 2013, now U.S. Pat. No. 9,181,299, which was a Rule 371 national stage filing of international application PCT/IB2012/051842 filed Apr. 13, 2012.

FIELD OF THE INVENTION

The present invention relates to the prevention and to the treatment of an infection of individuals with an HIV-1 virus.

BACKGROUND OF THE INVENTION

About 90% of the human HIV infections are caused by a HIV-1 virus. Human immunodeficiency virus type 1 (HIV-1) is characterized by a striking genetic variability caused by accumulation of mutations, arising during viral replication, and also caused by the recombination events. Long term failure of chemotherapeutic methods of HIV treatment are notably explained by the high mutagenic activity of HIV-1 viral strains. It was shown earlier that resistant viral variants quickly have been arisen in patients after different courses of antiretroviral therapy and even after multidrug therapy (HAART). These resistant viruses bear specific alterations in their proteins conformation and structure. Usually such mutations responsible for HIV-1 escape from current treatments are maintained through the successive virus generations and accumulate, as a result of selection under the treatment conditions.

Treatment with anti-HIV-1 medicines does not totally block replication of the virus, which allows a selection and accumulation of pre-existing resistance mutations, as well as of newly occurring mutations, thus bringing new opportunities for the virus to go on spreading. The existing antiretroviral medicines (NRTI, NNRTI, protease inhibitors, fusion inhibitors and mixtures thereof, like HAART) can only slow down the HIV-1 replication for a more or less prolonged period of time, until the arising and propagation of resistant viral strains. The wide spreading of HIV-1 resistant variants raises serious concerns and requires the availability for further anti-HIV-1 therapeutic tools.

Various anti-HIV therapeutic strategies, other than those making use of chemical anti-retroviral substances, have been considered, which include (i) the use of anti-HIV antibodies, (ii) HIV particles disruption-based vaccines, (iii) HIV peptides-based vaccines and (iv) DNA plasmid or viral vector-based vaccines, each having their specific drawbacks.

As the HIV pandemic continues to infect millions of people each year, the need for an effective vaccine increases. The development of anti-HIV vaccines has been deeply impaired, due to the difficulty in developing an immunogenic product capable of eliciting broadly neutralizing anti-HIV antibodies.

Induction of broadly neutralizing antibodies (bNAb) against primary isolates of human immunodeficiency virus (HIV) remains a major and unmet goal for AIDS vaccine research. Early attempts using envelope-based vaccines have elicited antibodies that are effective only against laboratory-adapted isolates. In these instances, protection has been correlated with high titer bNAb directed to the V3 hypervariable region of gp120. However, neutralizing activities generated are largely isolate-specific and are minimally effective against most primary isolates of HIV-1. The failure of subunit gp120 vaccines to protect against HIV-1 acquisition in Phase III clinical trials underscores the difficulty of the task.

Nevertheless, bNAb can often be found in HIV infected individuals. Responses generated early in infection are usually narrow in specificity, neutralizing the transmitted viruses in the host, but not the contemporaneous ones. Such responses broaden during the course of infection in some long-term survivors who are able to control their infection in the absence of antiviral treatment. However, the nature of the cross-neutralizing antibody response and the mechanisms leading to its genesis are not understood.

Naturally, NAbs against Env are generated within weeks after infection, but this early response is only efficient against a specific viral subtype; however, bNAbs (cross-reactive neutralizing Abs) can develop during the course of HIV. Recently several major studies have shown that approximately 25% of HIV-infected subjects (infected for at least 1 yr) have bNAb response, and 1% of "Elite neutralizers" with very robust activity against a great majority of clades. Importantly, these results demonstrate the ability of the immune system of infected persons to in vivo generate NAbs against HIV-1, during the course of the disease. They also suggest that broadly reactive Nab activities seem to develop over time and are fostered by chronic antigen exposure, in absence of knowledge about the titer of bNAbs that would be protective.

Persistent viral replication, in low noise, leads to a continuous evolution of Env to evade NAbs. Such antigenic evolution may focus new vaccine strategy on the more conserved region of the Env protein, and suggest that vaccine immunogens could be designed to mimic key highly conserved epitopes.

One of the major obstacles to the design of efficient anti-HIV vaccines has been that the target of bNAbs is the viral envelope protein (Env), which is highly variable, whereas the conserved elements seem to be poorly immunogenic. This means that kinetic and special constraints impede bNAbs from accessing potentially vulnerable sites during receptor binding and fusion processes. Actually few amount of NAbs have been described. For example, the first bNAb identified was b12, which occludes the CD4 binding site on gp120 and prevents CD4 attachment. The gp41 subunit is far more conserved than is gp120 involving conformational rearrangements is common to all stains. Very little bNAb activities are elicited against conserved structural elements of the gp41 that are shielded, difficult to access or transient; those bNAbs, including 2F5 and 4E10, targets the membrane-proximal ectodomain region (MPER) of gp41. However, immunization with these key epitopes did not result in the generation of bNAb activity. This dichotomy between the antigenic and immunologic characteristics is still not understood.

There is still a need in the art for therapeutic tools aimed at preventing or treating an infection caused by an HIV-1 virus.

SUMMARY OF THE INVENTION

The present invention relates to an immunogenic composition comprising an antigenic peptide of formula (I) below:

Nt-S-X1-X2-X3-K-X4-Ct (I) [Nt-SEQ ID No 1-Ct], wherein
Nt consists of a peptide having from 0 to 100 amino acids in length,
Ct consists of a peptide having from 0 to 100 amino acids in length,
each of X1 to X4 consists of an amino acid residue, wherein:
(i) X1 means the specific amino acid W or (ii) X1 means any amino acid residue excepted W,
(i) X2 means the specific amino acid S or (ii) X2 means any amino acid residue excepted S,
(i) X3 means the specific amino acid N or (ii) X3 means any amino acid residue excepted N,
(i) X4 means the specific amino acid S or (ii) X4 means any amino acid residue excepted S,
with the proviso that
three out of the four amino acid residues X1, X2, X3 and X4 mean the specific amino acid defined in their respective meaning (i) above, and
the remaining amino acid residue among X1 to X4 means any amino acid residue excepted the specific amino acid residue defined in its meaning (i),
provided that the peptide of formula (I) does not mean the peptide of SEQ ID No 18 disclosed in the PCT application filed on 22 Jun. 2010 under no PCT/US2010/001784 and published on 13 Jan. 2011 under no WO 2011/005289 in the name of President and Fellows of Harvard College.

This invention also deals with an immunogenic composition comprising an antigenic peptide of formula (I) as described above, for use as a medicament.

The present invention also concerns an immunogenic composition comprising an antigenic peptide of formula (I) as described above, for use in a method of preventing and/or treating an infection of an individual with an HIV-1 virus.

This invention also pertains to the use of an immunogenic composition comprising an antigenic peptide of formula (I) as described above, for manufacturing a medicament for preventing and/or treating an infection of an individual with an HIV-1 virus.

In certain embodiments, the meaning (ii) of one or more of X1, X2, X3 and X4 is selected, one independently from each other, from the group of amino acid residues consisting of Cysteine (Cys or C), Alanine (Ala or A), Glycine (Gly or G) and Valine (Val or V), Proline (Pro or P), and most preferably Alanine.

In certain embodiments, only one of X1 to X4 means an amino acid residue other than W (for X1), S (for X2), N (for X3) and S (for X4), respectively.

In certain embodiments, the antigenic peptide of formula (I) is selected from the group consisting of:

```
PWNASASNKSLDDIW  (SEQ ID No 12),

PWNASWANKSLDDIW  (SEQ ID No 13),

PWNASWSAKSLDDIW  (SEQ ID No 14),
and

PWNASWSNKALDDIW  (SEQ ID No 15),
```

This invention also pertains to an immunogenic composition comprising an antigenic peptide of formula (I).

In certain embodiments, the antigenic peptide of formula (I) is covalently linked to a carrier molecule.

In certain embodiments of the said immunogenic composition, the antigenic peptide of formula (I), optionally linked to a carrier molecule, is combined with one or more immuno-adjuvant agents.

The present invention also concerns a peptide of formula (I) as described in the present specification.

The invention also deals with the use of antibodies directed against a peptide of formula (I) for manufacturing a medicament for preventing and/or treating an individual infected with a HIV-1 virus.

This invention also relates to antibodies directed against a peptide of formula (I) above.

This invention also pertains to HIV-1 diagnosis methods, as well as HIV-1 diagnosis kits, that make use of a peptide of formula (I).

This invention also relates to HIV-1 prognosis methods, as well as HIV-1 prognosis kits, that make use of a peptide of formula (I).

It also concerns methods for monitoring the status of a HIV-1 infection that make use of a peptide of formula (I), especially in patients receiving an anti-HIV-1 medical treatment, as well kits for performing such monitoring methods.

DESCRIPTION OF THE FIGURES

FIG. 1 Amino acid sequence alignment of several peptides of formula (I).

Figure 2A:
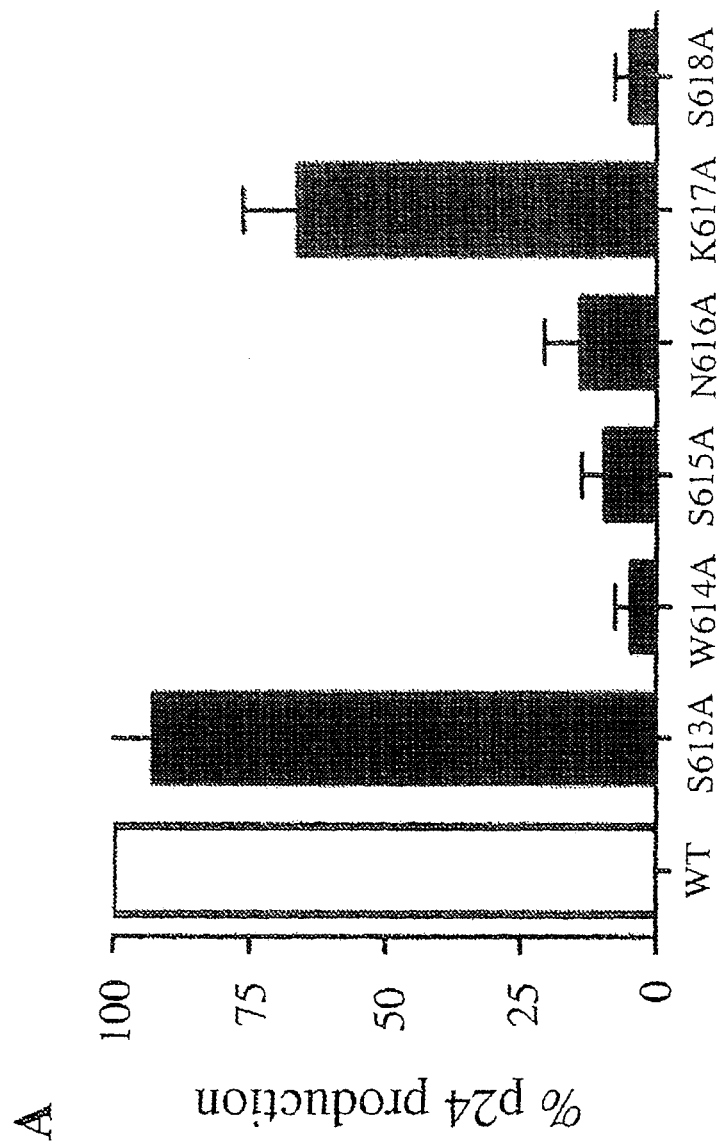

Wild type: amino acid sequence contained in the gp41 protein of the HIV-1 HXB2 strain, which may also be termed "3S".

S613A (M1) and K617A (M5): amino acid sequences having strong amino acid identity with "Wild type" above.

W614A, S615A, N616A and S618A: specific embodiments of a peptide of formula (I).

FIG. 2A-D. Infectivity of HIV-1 NL4.3 virus containing Alanine-substitution in the 3S/gp41 motif.

MT-2 cells were infected with 100 ng/mL of p24 equivalent antigen from wild-type (WT, open bars), or alanine-mutated 3S/gp41 (black bars) NL4.3 viruses.

(A) p24 antigen was quantified at day-6 post-infection. The results, expressed in relative units to the wild-type, represent the mean±SD from three to seven independent plasmid-clone preparations, depending of the mutants.

(B) Syncytium formation was quantified at day-4 post-infection by standard phase contrast microscopy. The results, expressed in relative units to the wild type, represent the mean±SD from two to four separated plasmid clone preparations, depending of the mutants.

(C) Kinetic study of p24 antigen production in the cell-supernatant of primary CD4+ T cells infected by wild type (WT, X) or alanine-mutated 3S/gp41 NL4.3 virus including S613A (■), W614A (Δ), S615A (◊), N616A (○), K617A (●), and S618A (□). This experiment is representative of 2 independent experiments managed with separated plasmid-clone preparations on purified CD4+ T cells from two independent healthy donors.

(D) Infectivity of Hela P4C5 cells by wild-type (WT, open bar) or alanine-mutated 3S/gp41 (black bars) NL4.3 virus. Cells were infected in triplicate with 4 ng/15,000 cells of p24 equivalent antigen for 48 h, and the (β-galactosidase activity was determined in the cell extracts. The results, expressed in relative units to the wild type, represent the mean±SD from three to four independent plasmid-clone preparations. Alanine-mutated NL4.3 viruses are referred as: S613A, W614A, S615A, N616A, K617A, and S618A.

FIG. 3A-D. Expression of NKp44L on CD4+ T cells and NK-cell degranulation mediated by 3S/gp41 alanine-mutants.

(A) Purified CD4+ T cells were non-infected (dotted lines), over night infected (black lines) with wild type (WT) or various alanine-mutated NL4.3 virus. Cells were stained with ligands for the NCRs (NKp30-Ig, NKp44-Ig or NKp46-Ig fusion-proteins). Histograms were gated on the CD4+ T cells. Overlay shown expression of NCR ligands on HIV-infected cells compared to non-infected cells. Numbers correspond to the proportion of CD4+ T cells positively expressing NCR ligands.

(B) Expression of NKp44L on purified CD4+ T cells were untreated (UT) or treated with peptides from the wild-type (WT) or the alanine-mutated 3S/gp41 synthetic peptides of the 3S/gp41 motif. Cells were either stained with anti-NKp44L mAb, or IgM isotype control (dotted lines). Histograms were gated on the CD4+ subset. Overlay shown expression of NKp44L, as compared to isotype control. Numbers correspond to the proportion of CD4+ T cells expressing NKp44L.

(C) Degranulation activity was assessed on IL2-activated NK cells against autologous CD4+ T cells, at an E/T ratio: 1/1, in the presence of anti-CD107a mAb. Purified CD4+ T cells were non-infected (NI), or over night infected with wild-type (WT) or alanine-mutated 3S/gp41 NL4.3 viruses. Dotted plot are gated one CD3−CD56+ NK cells in function of the expression of NKp44, and CD107a. Number in each panel corresponds to the proportion of positives NK cells.

(D) Degranulation efficacy of NK cells against autologous purified CD4+ T cells at an E/T ratio: 1/1, in the presence of anti-CD107a mAb. CD4+ T cells were untreated (UT) or treated with peptides from the wild-type (WT) or alanine-mutated synthetic peptides from the 3S/gp41 motif. CD4+ T cells were incubated with autologous IL2-activated NK cells Histograms were gated on the CD3−CD56+ NK cells expressing NKp44. Overlay shown expression of CD107a on NK cells tested in the presence of autologous CD4+ T cells treated with either wild-type (WT), or Alanine mutated 3S/gp41 synthetic peptides, as compared to untreated cells. Numbers correspond to the proportion of NK cells expressing CD107a. Alanine-mutated NL4.3 viruses or 3S/gp41 peptides are referred as S613A, W614A, S615A, N616A, K617A, and S618A.

FIG. 4A-D. Neutralization of viral infection and Inhibition of NKp44L on CD4+ T Cells and NK-cell degranulation by murine Ig generated from specific 3S/gp41 alanine-mutants.

Purified CD4+ T cells were infected with NL4.3 (left panel) or NDK (right panel) competent-viruses pre-incubated for 30 min with purified Ig providing from mice immunized with adjuvant alone (Ig-Adj, ♦), wild type (WT, X) or alanine-mutated 3S/gp41 NL4.3 virus including S613A (■), W614A (Δ), S615A (◊), N616A (○), K617A (●), and S618A (□).

(A) Competent-Viruses (200TCID$_{50}$) were incubated with various concentration ranged from 0 and 20 µg/ml of purified Ig for 30 min, followed by addition of PHA-activated purified CD4+ T cells. At Day 6 post-infection, p24 antigen was quantified in the cell-supernatant.

(B) Time-dependent effect. Competent-viruses (200TCID$_{50}$) were incubated with 10 µg/ml of Ig for 30 min followed by addition of PHA-activated purified CD4− T cells. Level of p24 was tested in the cell-supernatant every 2 days for 10 days post-infection.

(C) Expression of NKp44L on CD4− T cells was determined 17 h post-infection. Histograms were gated on the CD4+ cell subset. Overlay shown expression of NKp44L, as compared to IgM isotype control. Numbers correspond to the proportion of positives cells.

(D) Degranulation of autologous NK cells. CD4+ T cells were incubated with autologous NK cells at an E/T ratio: 1/1, in the presence of anti-CD107a mAb. Dotted plot are gated on CD3−CD56+ NK cells in function of the expression of NKp44, and CD107a. Number in each panel corresponds to the proportion of positives cells. Alanine-mutated NL4.3 viruses or 3S/gp41 peptides are referred as S613A, W614A, S615A, N616A, K617A, and S618A.

FIG. 5A-D. Neutralization of viral infection and Inhibition of NKp44L on CD4+ Cells and NK-cell degranulation by immuno-precipitated anti-W614A Ab purified from HIV-infected patients.

PHA-activated CD4+ T cells were infected with NL4.3 (left panel) or NDK (right panel) competent-viruses pre-incubated for 30 min with anti-3S-WT mAb (Anti-3S, ○), anti-3S-WT-immuno-purified Ab providing from 1 HIV-infected patient (#117, □), or anti-3S-W614A-immuno-purified Ab providing from 5 HIV-infected patients: #24 (●), #44 (■), #65 (▲), #71 (▼), and #109 (♦).

(A) Competent-viruses (200TCID$_{50}$) were incubated with various concentration ranged from 0 and 2 µg/ml of immuno-purified Ab for 30 min, followed by addition of CD4+ T cells. At Day 6 post-infection, p24 antigen was quantified in the cell-supernatant.

(B) Time-dependent effect. Competent-viruses (200TCID$_{50}$) were incubated with 1 µg/ml of immuno-purified Ab for 30 min followed by addition of PHA-activated purified CD4+ T cells. Level of p24 was tested in the cell-supernatant every 2 days for 10 days post-infection.

(C) Expression of NKp44L on CD4+ T cells was determined 17 h post-infection. Histograms were gated on the CD4+ T cell subset. Overlay shown expression of NKp44L, as compared to IgM isotype control. Numbers correspond to the proportion of positives cells.

(D) Degranulation of autologous NK cells. CD4+ T cells were incubated with autologous NK cells at an E/T ratio: 1/1, in the presence of anti-CD107a mAb. Dotted plot are gated on CD3−CD56+ NK cells in function of the expression of NKp44, and CD107a. Number in each panel corresponds to the proportion of positives NK cells. Alanine-mutated NL4.3 viruses or 3S/gp41 peptides are referred as S613A, W614A, S615A, N616A, K617A, and S618A.

Figure 6A:
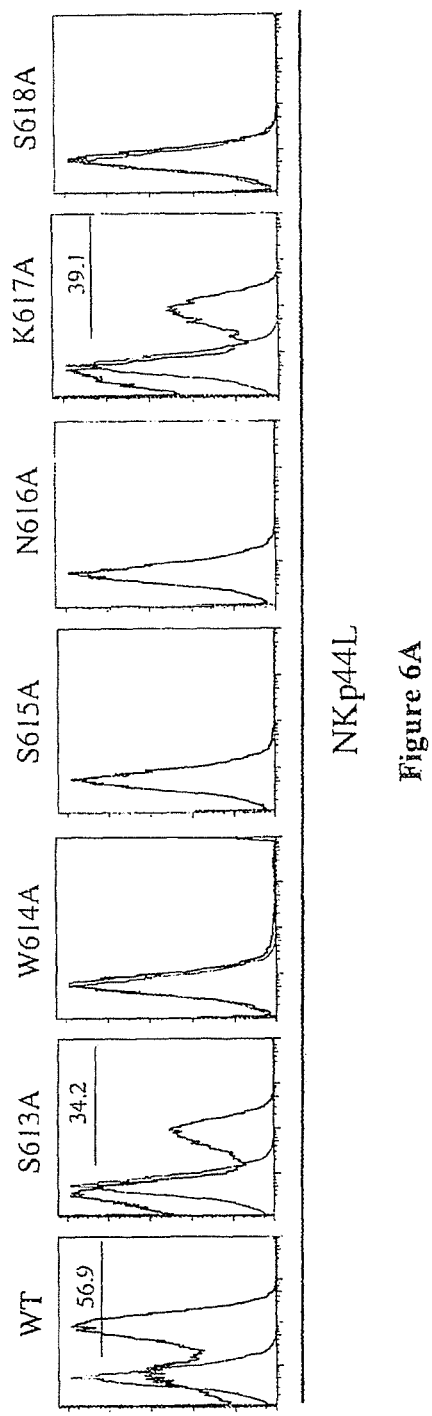
Figure 6B:
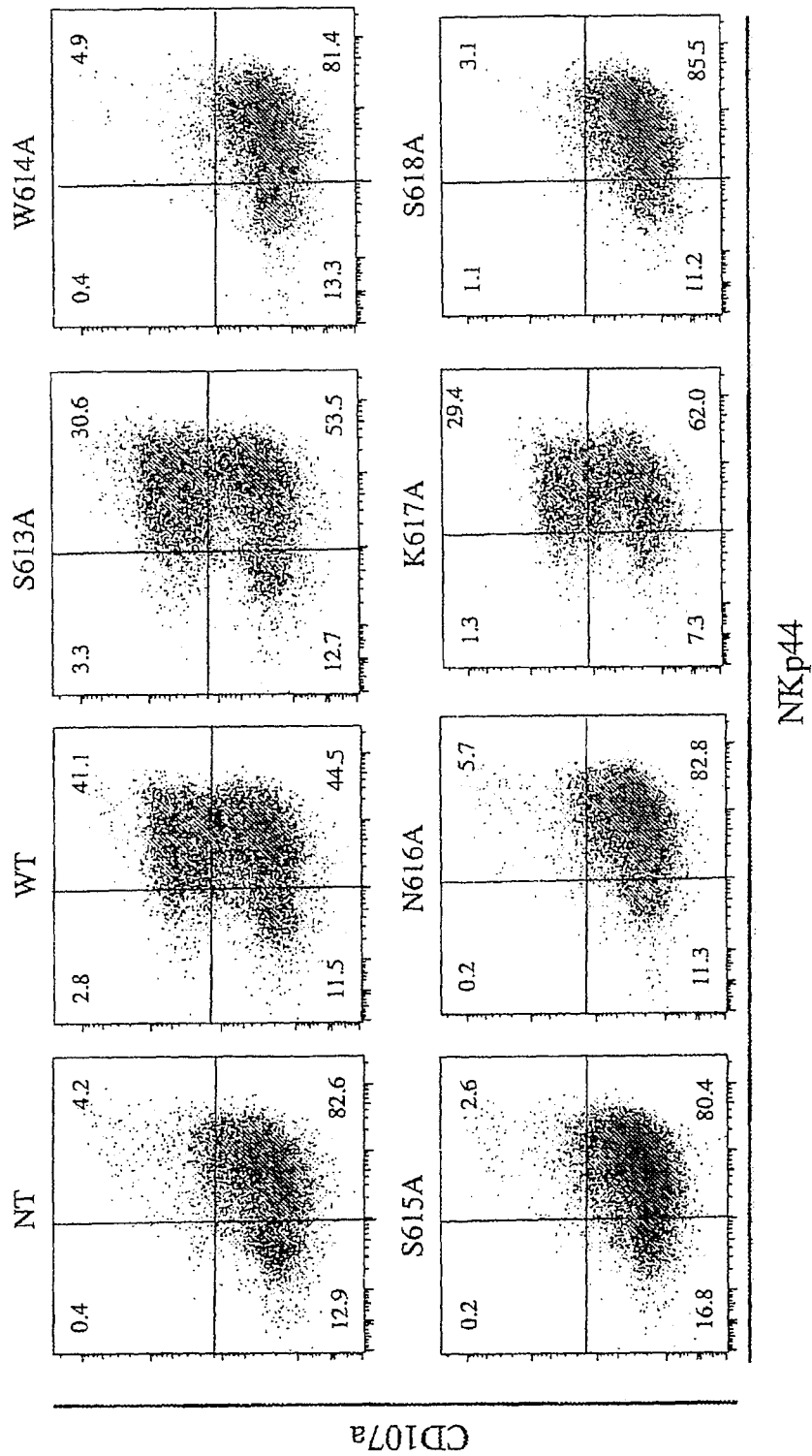

FIG. 6A-B. Expression of NKp44L, and degranulation of autologous NK cells, mediated by heat-inctivated alanine-mutants of 3S/gp41 on CD4+ T cells.

Purified CD4+ T cells were un-treated or treated over night with 100 ng p24 equivalent antigen per mL of heat-inactivated virus wild type (WT) NL4.3 virus or with the various alanine-mutants of 3S/gp41 viruses.

(A) Expression of NKp44L on CD4+ T cells was determined 17 h post-infection. Histograms were gated on the CD4+ T cell subset. Overlay shown expression of NKp44L, as compared to IgM isotype control. Numbers correspond to the proportion of positives cells.

(B) Degranulation of autologous NK cells. CD4+ T cells were incubated with autologous NK cells at an E/T ratio: 1/1, in the presence of anti-CD107a mAb. Dotted plot are gated on CD3−CD56+ NK cells in function of the expression of NKp44, and CD107a. Number in each panel corresponds to the proportion of positives NK cells. Alanine-mutated NL4.3 viruses or 3S/gp41 peptides are referred as S613A, W614A, S615A, N616A, K617A, and S618A.

DETAILED DESCRIPTION OF THE INVENTION

The present invention mainly provides anti-HIV-1 immunogenic or vaccine compositions, which immunogenic or vaccine compositions comprise specific antigenic peptides allowing, notably, the induction of broadly neutralizing anti-HIV-1 antibodies.

Ideally, an efficient HIV-1 vaccine would completely block infection. Actually, it may be more realistic to develop a suboptimal safe and efficient vaccine that both significantly reduces infection and prevents CD4+ T cells depletion. The main goal of this strategy is linked to the capacity to generate broadly neutralizing antibodies (bNAb) having also the capacity to act on CD4+ T cell depletion, which have seemed insurmountable in the prior art.

The present invention thus provides novel substances and compositions for preventing and/or treating the infection of a mammal organism, preferably of a human organism, by an HIV-1 virus.

It has been found according to the invention that a family of specific peptides which share a strong sequence identity with a known gp41-derived peptide named "3S", induce in vivo the production of anti-HIV-1 bNAb.

It is shown herein that these specific peptides raise a robust and broadly neutralizing activity against various HIV-1 virus clinical isolates, in contrast to known peptides derived from the gp41 HIV-1 protein, including the known "3S" peptide cited above.

Highly importantly, it has also been found according to the invention that these specific peptides do not trigger CD4+ T cell sensitivity to lysis by NK cells, although the whole functionalities of NK cells, including degranulation, remain intact.

Additionally, the inventors have shown that antibodies directed against these specific peptides block the CD4+ T cell sensitivity to NK cell lysis that is stimulated in the course of an infection with an HIV-1 virus.

The present invention relates to an immunogenic composition comprising an antigenic peptide of formula (I) below:

Nt-S-X1-X2-X3-K-X4-Ct  (I)  [Nt-SEQ ID No 1-Ct], wherein
  Nt consists of a peptide having from 0 to 100 amino acids in length,
  Ct consists of a peptide having from 0 to 100 amino acids in length,
  each of X1 to X4 consists of an amino acid residue, wherein:
    (i) X1 means the specific amino acid W or (ii) X1 means any amino acid residue excepted W,
    (i) X2 means the specific amino acid S or (ii) X2 means any amino acid residue excepted S,
    (i) X3 means the specific amino acid N or (ii) X3 means any amino acid residue excepted N,
    (i) X4 means the specific amino acid S or (ii) X4 means any amino acid residue excepted S,
    with the proviso that
      three out of the four amino acid residues X1, X2, X3 and X4 mean the specific amino acid defined in their respective meaning (i) above, and
      the remaining amino acid residue among X1 to X4 means any amino acid residue excepted the specific amino acid residue defined in its meaning (i), provided that the peptide of formula (I) does not mean the peptide of SEQ ID No 18 disclosed in the PCT application published as WO 2011/005289.

The peptide of SEQ ID No 18 disclosed in the PCT application published as WO 2011/005289 has the following amino acid sequence: "Ac-NHNHRIRTNPAIVK(Ac)TEN-SWSNKAKSICQQQ-NH$_2$" (SEQ ID No 16 of the present patent application)

A Nt peptide having from 0 to 100 amino acid residues in length encompasses peptides having 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 amino acid residues in length/

A Ct peptide having from 0 to 100 amino acid residues in length encompasses peptides having 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 amino acid residues in length/

As already mentioned above, a peptide of formula (I), when used in an immunogenic composition, preferably in combination with one or more immuno-adjuvant agents, induces the production of antibodies that block the infection of CD4+ T cells with HIV-1 viruses and/or block the spreading of HIV-1 virus to non-infected CD4+ T cells, as shown by the quasi-undetectable p24 production by the CD4+ T cells brought into contact both with the HIV-1 viruses and antibodies directed against a peptide of formula (I).

Further, in contrast to other HIV-derived peptides that have been used in the art as HIV antigens, including the "3S" peptide (shown in FIG. 1), a peptide of formula (I) does not trigger expression of NKp44L at the surface of the CD4+ T cells, and thus does not trigger destruction of CD4+ T cells by NK cells.

Still further, antibodies produced in an individual immunized with a peptide or formula (I) are able to block the NKp44L-mediated lysis of CD4+ T cells by NK cells, without impairing any other function of NK cells, which includes degranulation.

Thus, the present invention provides a highly efficient therapeutic tool that may be used for the prophylaxis and for the treatment of an infection with an HIV-1 virus.

An immunogenic composition which is used according to the invention comprises an antigenic peptide of formula (I) which, when the said immunogenic composition is administered to an individual, raises the production of antibodies directed against the said peptide of formula (I) which are endowed with neutralizing properties towards a plurality of clinical HIV-1 isolates, as shown in the examples herein. As it is illustrated further in the present specification, an antigenic peptide of formula (I) may be rendered immunogenic by conjugation to a carrier molecule and/or by combination with one or more immune-adjuvant agents.

An immunogenic composition comprising a polypeptide of formula (I) may be used prophylactically against an infection by an HIV-1 virus by inducing antibodies that drastically reduce or even block the infection of CD4 cells with the said HIV-1 virus.

An immunogenic composition comprising a polypeptide of formula (I) may be used for treatment purpose, in a HIV-1-infected individual, by inducing antibodies that drastically reduce or even block the infection of CD4+ T cells by HIV-1 viruses that have already replicated in the infected individual.

As shown in the examples herein, anti-HIV-1 antibodies that are obtained after immunization of a mammal with an immunogenic composition comprising an antigenic peptide of formula (I) consist of neutralizing antibodies that may possess an $IC_{50}$ of less than 20 µg/ml, in a CD4+ T cells-p24 assay.

Typically, a CD4+ T cells-p24 assay comprises the steps of:
a) preparing a test mixture by bringing into contact a replication-competent HIV-1 virus with a known amount of the antibodies to be tested,
b) incubating PHA-activated CD4+ T cells with the test mixture obtained at the end of step a), in the presence of IL-2, and
c) determining the p24 activity in the CD4+ T cell cultures obtained at the end of step b), and
d) determining the $IC_{50}$ value of the tested antibodies by comparing the p24 activity determined at step c) for the known amount of antibodies added at step a) with the p24 activity found in the same test where step a) is performed in the absence of anti-HIV antibodies.

Generally, for performing the neutralization assay described above, a serial of tests are performed where increasing known amounts of the tested antibodies are used in step a). A fully detailed description of the neutralisation assay is given in the examples herein.

The results obtained by the inventors show that an immunogenic composition comprising an antigenic peptide of formula (I) may be used with a high degree of safety for the individual in need thereof, since the said immunogenic composition does not cause undesirable side effects, and notably does not affect the CD4+ T cells functionality, in contrast to known anti-HIV antigenic peptides (e.g. the "3S" peptide shown in FIG. 1).

Further, an immunogenic composition comprising an antigenic peptide of formula (I) is a highly powerful anti-HIV therapeutic tool, due to its pleiotropic activities against an HIV-1 infection, including (i) the generation of antibodies endowed with a broadly neutralizing activity against a number of HIV-1 clinical isolates and (ii) the blocking of CD4+ T cells lysis by NK cells.

Still further, an immunogenic composition comprising an antigenic peptide of formula (I) is endowed with a high selectivity of action since, illustratively, it impairs exclusively the anti-CD4 activity of the NK cells, without affecting simultaneously an important antimicrobial immune resistance function of the NK cells, like degranulation.

Then, an immunogenic composition comprising an antigenic polypeptide of formula (I) (i) has an anti-HIV-1 activity by inducing broadly neutralizing anti-HIV-1 antibodies, and (ii) protects the functionality of the immune system of a HIV-1-infected individual by (a) protecting the CD4+ T cells from destruction and (b) ensuring that non-specific antimicrobial functions of the immune system remain fully functional.

Illustrative embodiments of peptides of formula (I) are disclosed in FIG. 1, which include (i) "W614A" or "M2" (SEQ ID No 12 herein), (ii) "S615A" or "M3" (SEQ ID No 13 herein), (iii) "N616A" or "M4" (SEQ ID No 14 herein) and (iv) "S618A" or "M6" (SEQ ID No 15 herein).

Importantly, as shown in the examples herein, other specific peptides having a strong amino acid identity with the peptides of formula (I), like those termed S613A (or"M1") and K617A (or "M5") represented in FIG. 1 are not endowed with any of the anti-HIV properties of the peptides of formula (I). Illustratively, the peptides S613A and K617A (i) do not induce anti-HIV neutralizing antibodies, (ii) trigger NKp44L expression by CD4 cells and thus also CD4+ T cells sensitivity to NK cells lysis and (iii) do not induce the production of antibodies able to reduce or block the CD4+ T cells sensitivity to lysis by NK cells.

Highly surprisingly, the inventors have shown that the peptides S613A and K617A discussed above induce antibodies that recognize well wild type sequences expressed by HIV-1 viruses, although these peptides are unable to induce neutralizing antibodies against HIV-1 viruses.

Also highly surprisingly, it is shown in the examples herein that the peptides of formula (I) induce antibodies that do not react with wild type sequences expressed by HIV-1 viruses, as shown in Table 4. These surprising results suggest that peptides of formula (I) are structurally distinct from the corresponding wild type HIV-1 sequences, although they induce broadly neutralizing anti-HIV-1 antibodies. These results are clearly in contrast to what the one skilled in the art would have expected when looking for antigenic compounds for inducing an efficient immune response against an infection by HIV-1 viruses.

On another hand, peptides having sequences close to a peptide of formula (I), like the above cited S613A and K617A peptides, appear to be structurally closely related to wild type HIV-1 sequences and are able to induce antibodies recognizing those wild type sequences, although these antibodies do not possess any anti-HIV-1 property.

The results reported herein show that nor (i) the safety of a peptide of formula (I) neither (ii) the various anti-HIV properties of the antibodies directed against a peptide of formula (I) could be anticipated by the one skilled in the art.

Further, it is expected that a peptide of formula (I) possesses a linear spatial structure.

The inventors have also shown that antibodies directed against a peptide of formula (I) may be found in a small number of individuals infected with an HIV-1 virus. A strong correlation has been found between (i) the presence of antibodies directed against a peptide of formula (I) in these HIV-1-infected individuals and (ii) a low HIV-1 viral load as well as a high number of CD4+ T cells. These results clearly indicate the high in vivo efficiency of antibodies directed against a peptide of formula (I) for preventing and/or treating the infection of an individual by a HIV-1 virus.

The examples herein also illustrate that mutated HIV-1 viruses encoding a mutated gp41 protein bearing one of the mutations W614A and S618A, that are present in embodiments of peptides of formula (I), have a highly reduced ability to infect a human lymphoblastoid cell line and do not trigger NKp44L expression by CD4+ T cells. These results suggest that the inability of a peptide of formula (I) to induce NKp44L expression by CD4+ T cells is also found in whole HIV-1 viruses expressing specific variant gp41 proteins.

As used herein, preventing or treating an infection of an individual with an HIV-1 virus encompasses (i) preventing or treating a disease linked to an infection of the said individual with an HIV-1 virus, including AIDS and (ii) preventing progression of HIV-1 disease.

As used herein, the term "HIV infection" generally encompasses infection of a host animal, particularly a human host, by the type 1 human immunodeficiency virus (HIV-1). "HIV-1" can be used herein to refer to any strains, forms, subtypes, clades and variations in the HIV-1 family. Thus, treating HIV-1 infection will encompass the treatment of a person who is a carrier of any of the HIV-1 family of retroviruses or a person who is diagnosed of active AIDS, as well as the treatment or prophylaxis of the AIDS-related conditions in such persons. A carrier of HIV-1 may be identified by any methods known in the art. For example, a person can be identified as an HIV-1 carrier on the basis that the person is anti-HIV-1 antibody positive, or is HIV-1-positive, or has symptoms of AIDS. That is, "treating HIV-1 infection" should be understood as treating a patient who is at any one of the several stages of HIV-1 infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating CD4+ T cells), and AIDS (which is defined by more serious AIDS-defining illnesses and/or a decline in the circulating CD4 cell count to below a level that is compatible with effective immune function). In addition, "treating or preventing HIV-1 infection" will also encompass treating suspected infection by HIV-1 after suspected past exposure to HIV-1 by e.g., contact with HIV-1-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter.

The term "treating HIV-1 infection" should also be understood in the context of anti-retroviral therapies, whether the patients are totally responsive or partially responsive to such therapies in terms of viral load and/or CD4 T cell count.

The term "preventing HIV-1 infection" may encompass treating a person who is free of HIV-1 infection but is believed to be at risk of infection by HIV-1, sooner or later.

The term "treating AIDS" means treating a patient who exhibits more serious AIDS-defining illnesses and/or a decline in the circulating CD4+ T cell count to below a level that is compatible with effective immune function. The term "treating AIDS" also encompasses treating AIDS-related conditions, which means disorders and diseases incidental to or associated with AIDS or HIV-1 infection such as AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia purpurea and associated opportunistic infections such as *Pneumocystis carinii* pneumonia, *Mycobacterial tuberculosis*, esophageal candidiasis, toxoplasmosis of the brain, CMV retinitis, HIV-related encephalopathy, HIV-1-related wasting syndrome, etc.

Thus, the term "preventing AIDS" as used herein means preventing in a patient who has HIV-1 infection or is suspected to have HIV-1 infection or is at risk of HIV-1 infection from developing AIDS (which is characterized by more serious AIDS-defining illnesses and/or a decline in the circulating CD4+ T cell count to below a level that is compatible with effective immune function) and/or AIDS-related conditions.

Thus, the terms "preventing progression of HIV-1" as used herein means preventing in a patient who has an HIV-1 infection, the decrease of its CD4+ T cell count and/or preventing the increase of its viral load, the two main markers linked to the complication of the disease and to an increase severity of the disease.

As used herein, amino acid residues encompass Alanine (also termed "A" or "Ala"), Arginine (also termed ("R" or "Arg"), Asparagine (also termed "N" or "Asn"), Aspartic acid (also termed "D" or "Asp"), Cysteine (also termed "C" or "Cys"), Glutamine (also termed "Q" or Gln"), Glutamic acid (also termed ("E" or "Glu"), Glycine (also termed "G" or "Gly"), Histidine (also termed "H" or "His"), Isoleucine (also termed "I" or "Ile"), Leucine (also termed "L" or "Leu"), Lysine (also termed "K" or "Lys"), Methionine (also termed "M" or "Met"), Phenylalanine (also termed ("F" or "Phe"), Proline (also termed "P" or "Pro"), Serine (also termed "S" or "Ser"), Threonine (also termed "T" or "Thr"), Tryptophan (also termed "W" or "Trp"), Tyrosine (also termed "Y" or "Tyr") and Valine (also termed "V" or "Val").

All amino acids in the peptides of the invention can be in both D- or L-form, although the naturally occurring L-form is preferred.

Thus, in a peptide of formula (I) above, when the amino acid residue X1 means (ii) any amino acid residue excepted W, then the amino acid residue X1 may mean any one of the amino acid residues A, R, N, D, C, Q, E, G, H, I, L, K, M, F, P, T, S, Y or V. The same reasoning is used for the meanings of any of the X1, X2, X3 and X4 amino acid residues of the antigenic peptide of formula (I).

Without wishing to be bound by any particular theory, the inventors believe that a peptide of formula (I) is spatially linear when suspended in a physiologically compatible saline solution (e.g. a 0.15 M NaCl solution).

Thus, in some embodiments of a peptide of formula (I), meaning (ii) of each of the amino acid residues X1, X2, X3 and X4 consists of an amino acid residue that does not generate a spatial conformation change, as compared with the amino acid residue of meaning (i) of X1, X2, X3 and X4, respectively.

In some embodiments of a peptide of formula (I), meaning (ii) of each of the amino acid residues X1, X2, X3 and X4 consists of a small size, uncharged, amino acid residue.

In some embodiments of a peptide of formula (I), meaning (ii) of each of the amino acid residues X1, X2, X3 and X4 is selected from the group consisting of Alanine (Ala or A), Cysteine (Cys or C), Glycine (Gly or G) and Valine (Val or V).

In some embodiments of a peptide of formula (I), meaning (ii) of each of the amino acid residues X1, X2, X3 and X4 is selected from the group consisting of Alanine (Ala or A), Cysteine (Cys or C), Glycine (Gly or G), Valine (Val or V) and Proline (Pro or P).

In some preferred embodiments of a peptide of formula (I), meaning (ii) of each of the amino acid residues X1, X2, X3 and X4 consists of a small size, uncharged, amino acid residue having a non-polar side chain. Some preferred small size, uncharged, amino acid residues are selected from the group consisting of Glycine (Gly or G), Alanine (Ala or A), Valine (Val or V), Leucine (Leu or L), Isoleucine (Ile or I), Methionine (Met or M), Phenylalanine (Phe or F), Proline (Pro or P) and tryptophane (Trp or W). More preferably, small size, uncharged, amino acid residues having a non-polar side chain are selected from the group consisting of Glycine (Gly or G), Alanine (Ala or A), Valine (Val or V), Leucine (Leu or L), Isoleucine (Ile or I), Proline (Pro or P) and Methionine (Met or M). In other preferred embodiments, small size, uncharged, amino acid residues having a non-polar side chain are selected from the group consisting of Glycine (Gly or G), Alanine (Ala or A), Valine (Val or V), Leucine (Leu or L), Isoleucine (Ile or I) and Methionine (Met or M).

In some of these preferred embodiments, meaning (ii) of each of the amino acid residues X1, X2, X3 and X4 is selected from the group consisting of Alanine (Ala or A), Glycine (Gly or G) and Valine (Val or V).

In some preferred embodiments of a peptide of formula (I), meaning (ii) of each of the amino acid residues X1, X2, X3 and X4 consists of an Alanine residue (Ala or A).

In some embodiments of a peptide of formula (I), each of the four amino acid residues X1, X2, X3 and X4 denote its meaning (ii).

In some embodiments of a peptide of formula (I), three amino acid residues among X1, X2, X3 and X4 denote, one independently of the two others, its meaning (ii) and the fourth amino acid residue among X1, X2, X3 and X4 denotes its meaning (i).

In some embodiments of a peptide of formula (I), two amino acid residues among X1, X2, X3 and X4 denote, one independently of the other, its meaning (ii) and the two other amino acid residues among X1, X2, X3 and X4 denote, one independently of the other, their meaning (i).

In some preferred embodiments of a peptide of formula (I), only one amino acid residue among X1, X2, X3 and X4 denotes meaning (ii) and each of the other amino acid residues among X1, X2, X3 and X4 denotes its meaning (i).

Thus, in some preferred embodiments of a peptide of formula (I) above,

X1 denotes meaning (ii) above and each of X2, X3 and X4 denotes their respective meaning (i) above, or X2 denotes meaning (ii) above and each of X1, X3 and X4 denotes their respective meaning (i) above, or X3 denotes meaning (ii) above and each of X1, X2 and X4 denotes their respective meaning (i) above, or X4 denotes meaning (ii) above and each of X1, X2 and X3 denotes their respective meaning (i) above.

The embodiments above are most preferred since it is believed that a single amino acid change (i.e. a single amino acid residue denoting meaning (ii)) among X1, X2, X3 and X4 shall minimize the risk of a spatial conformation change as compared to a peptide wherein all of the X1, X2, X3 and X4 residues denote their respective meaning (i), and thus shall increase the chances to induce good anti-HIV properties, i.e. induce the production of neutralizing anti-HIV antibodies.

In yet further embodiments of an antigenic peptide of formula (I), the said antigenic peptide has an amino acid length not more than 200 amino acid residues. These embodiments encompass peptides of formula (I) having 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 and 200 amino acid residues in length. In some of these preferred embodiments, a peptide of formula (I) has from 10 to 26 amino acid residues in length, which includes from 15 to 20 amino acid residues in length.

A peptide of formula (I) as described herein can be produced by a known cloning technology or by chemical synthesis.

For example, DNA encoding a peptide of formula (I) is prepared by use of a cloning technology, and inserted into an autonomously replicable vector to prepare a recombinant DNA. The recombinant DNA is introduced into an appropriate host, such as *Escherichia coli, Bacillus subtilis, Actinomyces*, yeast, filamentous fungus, a plant cell, an insect cell and an animal cell, to obtain a transformant. From the cultured product of the transformant, a peptide containing a peptide of formula (I) can be obtained. Alternatively, DNA encoding a peptide of formula (I) is prepared and subjected to an acellular protein-synthesis system using wheat germ and a cell extract from *Escherichia coli*, to synthesize the peptide of the invention. In some embodiments where the peptide of formula (I) is linked to a carrier protein, then an immunogenic product consisting of a fusion protein containing both a peptide of formula (I) and the desired carrier protein may be synthesized by a recombinant DNA technique.

Moreover, using a customary chemical synthesis method for a peptide of formula (I), such as a "solid phase method" or "a liquid phase method", amino acids are successively connected and extended by dehydration/condensation.

Furthermore, when a peptide of formula (I) is linked to a desired peptide or polypeptide, e.g. a protein carrier molecule, an immunogenic product comprising the antigenic peptide of formula (I) can be synthesized.

A peptide of formula (I) encompasses the following antigenic peptides:

```
Nt-S-X-S-N-K-S-Ct (Ia) - (Nt-SEQ ID No2-Ct),

Nt-S-W-X-N-K-S-Ct (Ib) - (Nt-SEQ ID No 3-Ct),

Nt-S-W-S-X-K-S-Ct (Ic) - (Nt-SEQ ID No 4-Ct),
and

Nt-S-W-S-N-K-X-Ct (Id) - (Nt-SEQ ID No 5-Ct),
``` wherein:

Nt and Ct have the same meaning as for the peptide of formula (I) defined above, and X is any amino acid residue excepted: W for (Ia), S for (Ib), N for (Ic) and S for (Id).

In certain embodiments of a peptide of formula (I), the said "any amino acid residue" is an alanine residue (also termed "A"). In those embodiments, the amino acid residue "X" of each of the peptides of formulae (Ia) to (Id) means "A".

In preferred embodiments, the peptide of formula (I) is selected from the group consisting of:

```
Nt-SASNKS-Ct (Nt-SEQ ID No 6-Ct),

Nt-SWANKS-Ct (Nt-SEQ ID No 7-Ct),

Nt-SWSAKS-Ct (Nt-SEQ ID No 8-Ct),
and

Nt-SWSNKA-Ct (Nt-SEQ ID No 9-Ct),
```

In certain embodiments of an antigenic peptide of formula (I), Nt (for "N-terminal" region) consists of a peptide having from 1 to 10 amino acid residues in length, which includes from 1 to 5 amino acid residues in length. Thus, according to these embodiments, Nt is a peptide having 1, 2, 3, 4, 5, 6, 7, 8, 9 or 10 amino acid residues in length. In some embodiments, Nt has 5 or 6 amino acid residues in length.

In certain embodiments of a peptide of formula (I), Nt comprises, or alternatively consists of, the amino acid sequence NH$_2$-PWNA-COOH [SEQ ID No 10].

In certain embodiments of an antigenic peptide of formula (I), Ct (for "C-terminal" region) consists of a peptide having from 1 to 10 amino acid residues in length, which includes from 1 to 5 amino acid residues in length. Thus, according to these embodiments, Ct is a peptide having 1, 2, 3, 4, 5, 6, 7, 8, 9 or 10 amino acid residues in length. In some embodiments, Ct has 5 or 6 amino acid residues in length.

In certain embodiments of a peptide of formula (I), Ct comprises, or alternatively consists of, the amino acid sequence NH$_2$-LDDIW-COOH [SEQ ID No 11].

Each of the Nt and Ct peptides are directly linked by a covalent bond to the corresponding end of the peptide S-X1-X2-X3-K-X4, preferably by a conventional peptide bond.

In an immunogenic composition according to the invention, one of the Nt or Ct peptides, or both of them, may comprise, or consist of, a polymer of a single amino acid monomer. Illustratively, the said amino acid polymer may consist of a poly-alanine, a poly-glutamine or a poly-lysine polymer.

The C- and/or N-terminal ends of a peptide of formula (I) could deviate from the natural sequences expressly specified herein by modification of the terminal NH$_2$-group and/or COOH-group and/or by modification of a NH$_2$ group and/or a COOH group of a lateral chain of an amino acid residue contained therein. These groups may for instance be acylated, acetylated, amidated or modified to provide a binding site for a carrier molecule.

In certain embodiments, the antigenic peptide is selected from the group consisting of:

```
PWNASASNKSLDDIW (SEQ ID No 12),

PWNASWANKSLDDIW (SEQ ID No 13),

PWNASWSAKSLDDIW (SEQ ID No 14),
and

PWNASWSNKALDDIW (SEQ ID No 15),
```

In certain embodiments of an immunogenic composition according to the invention, the antigenic peptide of formula (I) is covalently linked to a carrier molecule.

The types of carrier molecules used for generating an immunogenic product comprising a polypeptide of formula (I) linked to a carrier molecule are well in the general knowledge of the one skilled in the art. The function of the carrier molecule is to provide cytokine help (or T-cell help) in order to enhance the immune response against HIV-1.

The carrier molecule to which the peptide is optionally bound can be selected from a vide variety of known carriers. Examples of carrier molecules for vaccine purposes encompass proteins such as human or bovine serum albumin and keyhole limpet haemocyanin (KLH) and fatty acids. Other embodiments of carrier molecules to which an antigenic peptide of formula (I) may be covalently linked include bacterial toxins or toxoids, such as diphtheria, cholera, *E. coli* heat labile or tetanus toxoids, the *N. meninigitidis* outer membrane protein (European patent application no EP0372501), synthetic peptides (European patent applications no EP0378881 and no EP0427347), heat shock proteins (PCT application no WO93/17712), *Pertussis* proteins (PCT application n° WO98/58668), protein D from *H. influenzae* (PCT application no WO00/56360.) and toxin A or B from *C. difficile* (International patent application WO00/61761).

Any suitable conjugation reaction can be used, with any suitable linker where necessary. Examples herein illustrate embodiments of an immunogenic composition wherein peptides of formula (I) are covalently linked to a KLH carrier molecule.

The present invention also relates to an antigenic peptide of formula (I) as described herein, optionally covalently bound to a carrier molecule, for use as a medicament, including for use as an immunogenic active ingredient of a medicament.

This invention also deals with an antigenic peptide of formula (I) as described herein, optionally covalently bound to a carrier molecule, for use in a method for preventing and/or treating an infection of an individual with an HIV-1 virus.

The instant invention also pertains to the use of an antigenic polypeptide of formula (I), optionally covalently bound to a carrier molecule, for manufacturing a drug for preventing and/or treating an HIV-1-infected individual, i.e. for preventing and/or treating an infection of an individual with an HIV-1 virus.

The present invention also deals with a method for preventing and/or treating an individual infected with an HIV-1 virus, i.e. for preventing and/or treating an infection of an individual with an HIV-1 virus, comprising a step of administering an immunogenic composition comprising an antigenic peptide of formula (I), preferably linked to a carrier molecule, to the said individual.

In certain embodiments, an immunogenic composition used according to the invention comprises an antigenic peptide of formula (I) in an amount which is adapted to the administration of from 10 ng to 1 mg of a peptide of formula (I) to an individual in need thereof, for prophylactic of therapeutic purpose.

An amount of an antigenic peptide of formula (I) of from 10 ng to 10 mg encompasses an amount of peptide of formula (I) of about 20 ng, 30 ng, 40 ng, 50 ng, 60 ng, 70 ng, 80 ng, 90 ng, 100 ng, 150 ng, 200 ng, 250 ng, 300 ng, 350 ng, 400 ng, 450 ng, 500 ng, 550 ng, 600 ng, 700 ng, 800 ng, 900 ng, 1 µg, 2 µg, 3 µg, 4 µg, 5 µg, 6 µg, 7 µg, 8 µg, 9 µg, 10 µg, 20 µg, 30 µG, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 950 µg and 1 mg.

The amount of a peptide of formula (I) selected form the group of peptides of SEQ ID No 12, 13, 14 or 15 may be notably of about 200 µg, 500 µg or 1 mg.

The one skilled in the art may adapt the amount of a peptide of formula (I) easily by performing routine assays and determining the peptide amount range which, when administered in vivo induces an antibody response that block the infection of CD4+ T cells with a HIV-1 virus and/or block the spreading of a HIV-1 virus to non-infected CD4+ T cells, using known assays, including one or more of the assays disclosed in the examples herein.

Notably, the amount of peptide of formula (I) may vary depending of its amino acid length and thus depending on its molecular mass, it being taking into account that the ratio of the number of sequences "S-X1-X2-X3-K-X4" per weight of a peptide of formula (I) varies with the length of the Ct and Nt peptides contained in the said peptide of formula (I), and thus varies with the molecular mass of the said peptide.

Also, in the preferred embodiments wherein the antigenic peptide of formula (I) is bound to a carrier molecule, and wherein the patient is administered with an immunogenic compound comprising, or consisting of, the said peptide of formula (I) bound to the said carrier molecule, the amount of immunogenic peptide to be administered may vary with both (i) the molecular mass of the peptide of formula (I) and (ii) the molecular mass of the carrier molecule which is used.

The amount of an immunogenic compound to be administered to an individual is easily determined or adapted by the one skilled in the art, who is primarily guided by the effective amount range of a peptide of formula (I), which includes the effective amount range of a peptide of formula (I) selected from the group consisting of SEQ ID No 12-15), and then by the molecular mass of the immunogenic compound he intends to administer.

In some embodiments, the amount of immunogenic peptide to be administered may be of about 0.1 µg, 0.5 µg, 1 µg, 5 µg 10 µg or 20 µg of the said immunogenic compound.

The amount of a peptide of formula (I) may be of at most 10,000 mg of a peptide of formula (I).

The amount of a peptide of formula (I) specified above also apply when the said peptide of formula (I) is conjugated to a carrier molecule, in an immunogenic composition according to the invention.

Illustratively, when used in human individuals, an immunogenic composition comprising a peptide of formula (I) conjugated to the KLH carrier molecule may contain from 0.1 µg to 50 µg of the immunogenic product KLH-peptide of formula (I) conjugate.

In certain embodiments, an immunogenic composition is administered at least twice to an individual in need thereof. In these embodiments, the second step of administration of an immunogenic composition according to the invention is performed in a time period of from 2 weeks to 6 months after the first administration step.

In certain embodiments, an immunogenic composition is administered at least three times to an individual in need thereof. In these embodiments, the second step of administration of the said immunogenic composition according to the invention is performed in a time period of from 2 weeks to 6 months after the first administration step. In these embodiments, the third step of administration of the said immunogenic composition is performed in a time period of from more than 6 months to about one year after the first administration step.

In some embodiments, the said immunogenic composition is then again administered to an immunized individual, for example every 5 years time period or every 10 years time period.

The present invention also relates to immunogenic compositions comprising an antigenic polypeptide of formula (I) as described herein.

In certain embodiments, the antigenic peptide of formula (I) is covalently linked to a carrier molecule.

In certain embodiments, an immunogenic composition according to the invention further comprises one or more immuno-adjuvant agents.

An immunogenic composition as defined herein which comprises an immunogenic product comprising a peptide of formula (I), preferably an immunogenic product consisting of a conjugate between the said peptide of formula (I) and a carrier molecule, and which further comprises one or more immuno-adjuvant compounds, may also be termed a "vaccine composition" in the present specification.

In some embodiments, there is no specific distinction to be made between an immunogenic composition according to the invention and a vaccine composition according to the invention, beyond the terms employed to designate such compositions.

More precisely, an immunogenic composition is aimed at generating antibodies directed against a peptide of formula (I) when it is administered to a mammal organism, e.g. a mouse, a rabbit, a sheep, a horse or a goat organism, in situations wherein the generated antibodies are not expected to exert a preventive or a therapeutic effect in the immunized mammal organism Immunogenic compositions according to the invention may be used for producing antibodies directed against a peptide of formula (I), for a further non-therapeutic use of these antibodies, e.g. as a HIV-1 virus detection reagent or a HIV-1-derived peptide detection reagent.

On another hand, a vaccine composition according to the invention is aimed at generating antibodies directed against a peptide of formula (I) in the mammal organism to which the said vaccine composition is administered, in situations wherein the generated antibodies are not expected to exert a preventive or a therapeutic effect in the immunized mammal organism.

Immuno-adjuvant agents encompass, but are not limited to, Stimulon™, QS-21 (Aquila Biopharmaceuticals, Inc., Framingham, Mass.); MPL™ (3-O-deacylated monophosphoryl lipid A; Corixa, Hamilton, Mont.), 529 (an amino alkyl glucosamine phosphate compound, Corixa, Hamilton, Mont.), IL-12 (Genetics Institute, Cambridge, Mass.); GM-CSF (Immunex Corp., Seattle, Wash.); N-acetyl-muramyl-L-theronyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy-ethylamine) (CGP 19835A, referred to as MTP-PE); and cholera toxin. Other immuno-adjuvant agents or compounds which may be used encompass non-toxic derivatives of cholera toxin, including its A subunit, and/or conjugates or genetically engineered fusions of the *N. meningitidis* polypeptide with cholera toxin or its B subunit ("CTB"), procholeragenoid, fungal polysaccharides, including schizophyllan, muramyl dipeptide, muramyl dipeptide ("MDP") derivatives, phorbol esters, the heat labile toxin of *E. coli*, block polymers or saponins.

Illustratively, the examples herein illustrate a vaccine composition comprising (i) a conjugate between KLH and a peptide of formula (I) as the immunogenic product and (ii) the incomplete Freund's adjuvant as the immuno-adjuvant agent.

The formulation of such immunogenic compositions is well known to persons skilled in the art Immunogenic compositions of the invention preferably include a pharmaceutically acceptable carrier. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. The preparation and use of pharmaceutically acceptable carriers is well known in the art. Except insofar as any conventional media or agent is incompatible with the active ingredient, use thereof in the immunogenic compositions of the present invention is contemplated.

Such immunogenic compositions can be administered parenterally, e.g., by injection, either subcutaneously or intramuscularly, as well as orally or intranasally. Other modes of administration employ oral formulations, pulmonary formulations, suppositories, and transdermal applications, for example, without limitation. Oral formulations, for example, include such normally employed excipients as, for example, pharmaceutical grades of mannitol, lactose, starch, magnesium stearate, sodium saccharine, cellulose, magnesium carbonate, and the like, without limitation.

The present invention also pertains to a vaccine composition comprising an antigenic polypeptide of formula (I) described herein in combination with one or more immuno-adjuvant compounds.

The present invention also relates to vaccine composition comprising (i) an immunogenic product comprising a peptide of formula (I) which is combined with (ii) one or more immuno-adjuvant compounds.

Generally, an immunogenic or a vaccine composition according to the invention comprises 1, 2, 3, 4 or at most 5 distinct immuno-adjuvant compounds.

In preferred embodiments, an immunogenic or a vaccine composition according to the invention comprises 1 or 2 distinct immuno-adjuvant compounds.

In some preferred embodiments of an immunogenic or a vaccine compositin, the peptide of formula (I) is selected from the group consisting of:

```
Nt-SASNKS-Ct  (Nt-SEQ ID No 6-Ct),

Nt-SWANKS-Ct  (Nt-SEQ ID No 7-Ct),

Nt-SWSAKS-Ct  (Nt-SEQ ID No 8-Ct),
and

Nt-SWSNKA-Ct  (Nt-SEQ ID No 9-Ct),
```

In some preferred embodiments of an immunogenic or a vaccine composition, the antigenic peptide of formula (I) is selected from the group consisting of:

```
PWNASASNKSLDDIW  (SEQ ID No 12),

PWNASWANKSLDDIW  (SEQ ID No 13),

PWNASWSAKSLDDIW  (SEQ ID No 14),
and

PWNASWSNKALDDIW  (SEQ ID No 15),
```

In some preferred embodiments, the antigenic polypeptide of formula (I) is covalently linked to a carrier molecule.

The present invention also concerns an antigenic peptide of formula (I) as described extensively in the present specification, as the active agent of a vaccine composition aimed at preventing and/or treating a HIV-1-infected individual.

More generally, the present invention also relates to a peptide of formula (I) per se, as described extensively in the present specification.

Antibodies Directed Against a Peptide of Formula (I)

As it has been extensively discussed and experimentally illustrated herein, the immunisation of an individual with an immunogenic composition comprising a peptide of formula (I) induces the production of broadly neutralizing anti-HIV-1 antibodies. These broadly neutralizing anti-HIV-1 antibodies may be used themselves as active anti-HIV-1 agents.

The antibodies directed against a peptide of formula (I) may be used for HIV-1 prevention or HIV-1 therapeutic purposes, as well as for HIV-1 diagnosis purposes.

In some embodiments, antibodies directed against a peptide of formula (I) consist of antibodies produced following immunization of a mammal, including a human, with an immunogenic composition comprising a peptide of formula (I) as described herein.

In some embodiments, antibodies directed against a peptide of formula (I) are obtained from HIV-1-infected individuals who have raised an immune response against HIV-1.

In both embodiments above, the said antibodies may be obtained by purification from a sample, especially a blood sample, collected from the said mammal, including from the said human.

In both embodiments above, the said antibodies may also be obtained by cloning the relevant DNA material encoding them, starting for example from B cells obtained from the said mammal, including from the said human.

In both embodiments above, the said antibodies may also be obtained by sequencing the amino acid sequences of the said antibodies collected from the said mammal, including from the said human, and then synthesize a DNA molecule encoding the said antibody or a portion thereof comprising the CDR thereof, for producing relevant recombinant antibodies directed against a peptide of formula (I).

The present invention also deals with antibodies directed against a peptide of formula (I) as described herein.

In some preferred embodiments, the said antibodies are directed against a peptide of formula (I) selected from the group consisting of:

```
Nt-SASNKS-Ct (Nt-SEQ ID No 6-Ct),

Nt-SWANKS-Ct (Nt-SEQ ID No 7-Ct),

Nt-SWSAKS-Ct (Nt-SEQ ID No 8-Ct),
and

Nt-SWSNKA-Ct (Nt-SEQ ID No 9-Ct
```

In some other preferred embodiments, the said antibodies are directed against a peptide of formula (I) selected from the group consisting of:

```
PWNASASNKSLDDIW (SEQ ID No 12),

PWNASWANKSLDDIW (SEQ ID No 13),

PWNASWSAKSLDDIW (SEQ ID No 14),
and

PWNASWSNKALDDIW (SEQ ID No 15),
```

Preparing antibodies directed against a peptide of formula (I) by immunization with an immunogenic composition comprising a peptide of formula (I) is notably disclosed in the examples herein. Alternatively the antibodies directed against a peptide of formula (I) may be collected from HIV-1 infected patients already harbouring naturally such antibodies; they can also be obtained after immortalisation of the human B lymphocytes producing them; their cDNA can also be cloned and used further for producing them or their derivatives through recombinant DAN technology.

The present invention also deals with the use of anti-HIV-1 antibodies obtained from an individual immunized with an immunogenic composition described herein, for manufacturing a medicament for preventing and/or treating an HIV-1-infected individual.

The term "antibody" herein is used to refer to a molecule having a useful antigen binding specificity. Those skilled in the art will readily appreciate that this term may also cover polypeptides which are fragments of or derivatives of antibodies yet which can show the same or a closely similar functionality. Such antibody fragments or derivatives are intended to be encompassed by the term antibody as used herein. By "antibody" or "antibody molecule" for the purpose of passive immunotherapy, it is intended herein not only whole immunoglobulin molecules but also fragments thereof, such as Fab, F(ab')$_2$, Fv and other fragments thereof that retain neutralizing activity against HIV-1 viruses. Similarly, the term antibody includes genetically engineered derivatives of antibodies such as single chain Fv molecules (scFv) and domain antibodies (dAbs).

The manufacture of compositions comprising purified antibodies directed against a peptide of formula (I) is disclosed in the examples herein.

In some embodiments, an antibody directed against a peptide of formula (I) consist of a polyclonal antibody. Production of composition comprising purified polyclonal antibodies directed against a peptide of formula (I) is disclosed in the examples herein.

The term "monoclonal antibody" is used herein to encompass any isolated Ab's such as conventional monoclonal antibody hybridomas, but also to encompass isolated monospecific antibodies produced by any cell, such as for example a sample of identical human immunoglobulins expressed in a mammalian cell line.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al. (1984) Proc. Natl. Acad. Sci. USA 81, 6851-6855). That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the V.sub.H and V.sub.L partner domains are linked via a flexible oligopeptide (Bird et al (1988) Science 242, 423; Huston et al (1988) Proc. Natl. Acad. Sci. USA 85, 5879) and single domain antibodies (dabs) comprising isolated V domains (Ward et al (1989) Nature 341, 544). A general review of the techniques involved in the synthesis of antibody fragments which retain their specific binding sites is to be found in Winter & Milstein (1991, Nature 349, 293-299).

By "ScFv molecules" we mean molecules wherein the $V_H$ and $V_L$ partner domains are linked via a flexible oligopeptide. Engineered antibodies, such as ScFv antibodies, can be made using the techniques and approaches described in J. Huston et al, (1988) "Protein engineering of antibody binding sites: recovery of specific activity in an anti-digoxin single chain Fv analogue produced in *E. coli*", Proc. Natl. Acad. Sci. USA, 85, pp. 5879-5883, and in A. Pluckthun, (1991) "Antibody engineering; Advances from use of *E. coli* expression systems", Bio/technology 9 (6): 545-51, incorporated herein by reference.

Suitable monoclonal antibodies which are reactive as described herein may be prepared by known techniques, for example those disclosed in "Monoclonal Antibodies; A manual of techniques", H Zola (CRC Press, 1988) and in "Monoclonal Hybridoma Antibodies: Techniques and Application", S G R Hurrell (CRC Press, 1982).

A further embodiment encompasses humanised antibodies where the regions of the murine antibody that contacted the antigen, the Complementarity Determining Regions (CDRs) were transferred to a human antibody framework. Such antibodies are almost completely human and seldom cause any harmful antibody responses when administered to patients. Several chimeric or humanised antibodies have been registered as therapeutic drugs and are now widely used within various indications (Borrebaeck & Carlsson, 2001, Curr. Opin. Pharmacol. 1: 404-408).

It is preferred if the antibody is a humanised antibody. Suitably prepared non-human antibodies can be "humanised" in known ways, for example by inserting the CDR regions of mouse antibodies into the framework of human antibodies. Humanised antibodies can be made using the techniques and approaches described in Verhoeyen et al (1988) Science, 239, 1534-1536, and in Kettleborough et al, (1991) Protein Engineering, 14 (7), 773-783.

Other antibody embodiments encompass completely human antibodies, that may be produced using recombinant technologies. Typically large libraries comprising billions of different antibodies are used. In contrast to the previous technologies employing chimerisation or humanisation of e.g. murine antibodies this technology does not rely on immunisation of animals to generate the specific antibody. Instead the recombinant libraries comprise a huge number of pre-made antibody variants wherein it is likely that the library will have at least one antibody specific for any antigen.

In the passive treatments of an HIV-1 infection as provided herein, the antibodies of the present invention will be administered, preferably intravenously, to the patients in need thereof. The frequency of administration may be determined clinically by following the decline of antibody titres in the serum of patients over time, but in any event may be at a frequency of 1 to 52 times per year, and most preferably between 1 and 12 times per year. Quantities of antibody may vary according to the severity of the disease, or half-life of the antibody in the serum, but preferably will be in the range of 1 to 10 mg/kg of patient, and preferably within the range of 1 to 5 mg/kg of patient, and most preferably 1 to 2 mg/kg of patient.

HIV-1 Diagnosis, Prognosis, Monitoring Methods and Kits

As it is disclosed in the examples herein, antibodies directed against a peptide of formula (I) may be found in HIV-1-infected patients.

Consequently, a peptide of formula (I) may be used as a detection reagent for determining the presence of, and optionally the amount of, antibodies directed against the said peptide in a tested individual.

This invention relates to a method for detecting and/or quantifying antibodies directed against a peptide of formula (I) in a sample, comprising the following steps:
  a) bringing into contact a sample to be tested with one or more peptides of formula (I), and
  b) detecting and/or quantifying the formation of complexes between the said peptides of formula (I) and antibodies present in the said sample.

The present invention also concerns a kit for detecting and/or quantifying antibodies directed against a peptide of formula (I) in a sample, comprising:

a) one or more peptides of formula (I) thereon, and
b) one or more reagents for detecting complexes formed between the said peptides and antibodies present in the said sample.

In some embodiments, the sample to be tested consists of a sample previously collected form an individual, which includes (i) an individual who is suspected to be infected by an HIV-1 virus and (ii) an individual who has been infected by an HIV-1 virus.

In some embodiments, the said sample consists of a preparation expected to contain antibodies directed against a peptide of formula (I), such as (i) a preparation of antibodies purified from samples collected from a mammal immunized with an immunogenic composition comprising a peptide of formula (I) and (ii) a preparation of monoclonal antibodies or of recombinant antibodies directed against a peptide of formula (I).

In some embodiments of the detection method above, the peptide(s) of formula (I) is (are) immobilized on a substrate.

In some embodiments, a peptide of formula (I) may be used as a reagent for diagnosing the infection of an individual with an HIV-1 virus.

Thus, the present invention also concerns a method for the diagnosis of an infection with an HIV-1 virus in an individual, comprising the following steps:
a) bringing into contact a sample from the said individual with one or more peptides of formula (I), and
b) detecting formation of complexes between the said peptides of formula (I) and antibodies present in the said sample.

In some embodiments of step b) of the method, the complexes between the said peptides of formula (I) and antibodies, when present, are quantified.

This invention also relates to a kit for the diagnosis of an infection with an HIV-1 virus in an individual, comprising:
a) one or more peptides of formula (I), and
b) one or more reagents for detecting complexes formed between the said peptides of formula (I) and antibodies present in a sample collected from said individual.

In some embodiments of the diagnosis method or of the diagnosis kit above, the said peptide(s) of formula (I) is (are) immobilized on a substrate, as it is disclosed further in the present specification.

According to the method above, an HIV-1 infection is determined if the formation of complexes between the peptide(s) of formula (I) and antibodies contained in the sample previously collected from the tested individual are detected.

According to the diagnosis method above, the level of the immune response of a HIV-1-infected individual against an HIV-1 virus is determined by quantifying the complexes formed between the peptide(s) of formula (I) and antibodies contained in the sample previously collected from the tested individual.

In some embodiments, a peptide of formula (I) may be used as a reagent for performing a prognosis of progression of the infection of an individual with an HIV-1 virus.

Thus, the present invention also concerns a method for a prognosis of progression of an infection with an HIV-1 virus in an individual, comprising the following steps:
a) bringing into contact a sample from the said individual with one or more peptides of formula (I), and
b) detecting and quantifying the formation of complexes between the said peptides of formula (I) and antibodies present in the said sample.

This invention also relates to a kit for the prognosis of progression of an infection with an HIV-1 virus in an individual, comprising:
a) one or more peptides of formula (I), and
b) one or more reagents for detecting complexes formed between the said peptides of formula (I) and antibodies present in a sample collected from said individual.

According to the method above, an HIV-1 infection is determined if the formation of complexes between the peptide(s) of formula (I) and antibodies contained in the sample previously collected from the tested individual are detected.

According to the prognosis method above, the level of the immune response of a HIV-1-infected individual against an HIV-1 virus is determined at step b).

When performing the prognosis method above, a favourable outcome is expected when a high level of antibodies directed to a polypeptide of formula (I) is measured at step b). Conversely, a poor outcome is expected when a low level of antibodies directed to a polypeptide of formula (I) is measured at step b).

As used herein, a "high" level of antibodies directed against a peptide of formula (I) is determined by comparison with one or more reference values.

In some embodiments of the prognosis method above, a favourable outcome may be determined if the presence of antibodies directed against a peptide of formula (I) is detected in a sample previously collected from the said HIV-1-infected individual, since, as it is shown in the examples herein, individuals having serum antibodies directed against a peptide of formula (I) have been found to have good clinical parameters, such as a low viral load and high CD4+ T cell count.

The diagnosis method above, the prognosis method above, as well as the kits for performing the said methods, may be used for monitoring the efficiency of an anti-HIV-1 medical treatment in a HIV-1-infected individual.

This invention also relates to a method for monitoring an anti-HIV-1 medical treatment in a HIV-1-infected individual, comprising the steps of:
a) administering an anti-HIV-1 treatment to the said HIV-1-infected individual, and
b) determining the level of antibodies directed against a peptide of formula (I) in a sample collected from the said patient.

In some embodiments of the monitoring method, level of antibodies directed against a peptide of formula (I) is determined prior to administering an anti-HIV-1 treatment to the said individual, thus prior to step a) of the method.

In some embodiments of the monitoring method, especially when the anti-HIV-1 treatment comprises a plurality of steps of administering an anti-HIV-1 pharmaceutical composition to the said individual, the monitoring method above is performed at each administration step, or only at one or more administration steps or at after the last administration step.

It is herein specified that embodiments of the anti-HIV-1 medical treatment that may monitored according to the method above encompass immunization of the HIV-1-infected individual with a vaccine composition comprising a peptide of formula (I) as described herein.

Phrases such as "sample containing an antibody" or "detecting an antibody in a sample" are not meant to exclude samples or determinations (detection attempts) where no antibody is contained or detected. In a general sense, this invention involves assays to determine whether an antibody produced in response to infection and during the course the disease with a HIV-1 virus is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc) or the Examples herein.

The diagnostic method comprises taking a sample of body fluid or tissue likely to contain antibodies. The antibodies can be, e.g., of IgG, IgE, IgD, IgM, or IgA type.

Generally, IgM and/or IgA antibodies are detected, e.g. for the detection of early infection. IgG antibodies can be detected when some of the additional peptides discussed above are used in the method (e.g. peptides for the detection of flagellum proteins). The sample is preferably easy to obtain and may be serum or plasma derived from a venous blood sample or even from a finger prick. Tissue from other body parts or other bodily fluids, such as cerebro-spinal fluid (CSF), saliva, gastric secretions, mucus, etc. are known to contain antibodies and may be used as a source of the sample.

Once the peptide antigen and sample antibody are permitted to react in a suitable medium, an assay is performed to determine the presence or absence of an antibody-peptide reaction. Among the many types of suitable assays, which will be evident to a skilled worker, are immunoprecipitation and agglutination assays.

In embodiments of the invention, the assay may comprise (1) immobilizing the antibody(s) in the sample, adding a peptide of the invention, and then detecting the degree of antibody bound to the peptide, e.g. by the peptide being labelled or by adding a labelled substance (conjugate, binding partner), such as a labelled antibody, which specifically recognizes the peptide; (2) immobilizing a peptide of the invention, adding the sample containing an antibody(s), and then detecting the amount of antibody bound to the peptide, e.g. by adding a labelled substance (conjugate, binding partner), such as a labelled antibody, which specifically recognizes the antibody; or (3) reacting the peptide and the sample containing antibody(s) without any of the reactants being immobilized, and then detecting the amount of complexes of antibody and peptide, e.g. by the peptide being labelled or by adding a labelled substance (conjugate, binding partner), such as a labelled antibody, which specifically recognizes the peptide.

Immobilization of a peptide of the invention can be either covalent or non-covalent, and the non-covalent immobilization can be non-specific (e.g. non-specific binding to a polystyrene surface in e.g. a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin or an analogue thereof. An alternative is a situation in which the moiety has the amino acid sequence His-His-His-His-His-His (SEQ ID NO:11) and the carrier comprises a Nitrilotriacetic Acid derivative (NTA) charged with $Ni^{++}$ ions. Among suitable carriers, supports or surface are, e.g., magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In a preferred assay, a peptide of the invention is immobilized to the solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices, dipsticks and immunocapillary or immunochromatographic immunoassay devices.

In embodiments of the invention, the solid or semi-solid surface or carrier is the floor or wall in a microtiter well; a filter surface or membrane (e.g. a nitrocellulose membrane or a PVDF (polyvinylidene fluoride) membrane, such as an Immobilon membrane); a hollow fiber; a beaded chromatographic medium (e.g. an agarose or polyacrylamide gel); a magnetic bead; a fibrous cellulose matrix; an HPLC matrix; an FPLC matrix; a substance having molecules of such a size that the molecules with the peptide bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

In some embodiments of the invention, the peptide is provided with a suitable label which enables detection. Conventional labels may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or by flow cytometry (FACscan); detection of a radioactively labeled agent by autoradiography; electron microscopy; immunostaining; subcellular fractionation, or the like. In one embodiment, a radioactive element (e.g. a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody which binds to the first antibody. This secondary antibody can be labeled, e.g., with a radioactive, enzymatic, fluorescent, luminescent, or other detectable label, such as an avidin/biotin system.

In embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

In one embodiment of the method, the peptide, or a mixture of peptides, is electro- or dot-blotted onto nitrocellulose paper. Subsequently, the biological fluid (e.g. serum or plasma) is incubated with the blotted antigen, and antibody in the biological fluid is allowed to bind to the antigen(s). The bound antibody can then be detected, e.g. by standard immunoenzymatic methods.

In another embodiment of the method, latex beads are conjugated to the antigen(s) of the invention. Subsequently, the biological fluid is incubated with the bead/peptide conjugate, thereby forming a reaction mixture. The reaction mixture is then analyzed to determine the presence of the antibodies.

One preferred assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing anti-HIV-1 antibodies. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin from another animal, such as dog, mouse, cow, etc.) that is conjugated to an enzyme or other label by standard procedures and is dissolved in blocking buffer. The label can be chosen from a variety of enzymes, including horseradish peroxidase (HRP), beta-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD standard deviations (SDs) of at least 50 serum samples collected from individuals who are not infected by an HIV-1 virus, or by other such conventional definitions. In the case of a very specific assay, OD+2 SD can be used as a cutoff value.

In one embodiment of an ELISA, a peptide of the invention is immobilized on a surface, such as a ninety-six-well ELISA plate or equivalent solid phase that is coated with streptavidin or an equivalent biotin-binding compound at an optimal concentration in an alkaline coating buffer and incubated at 4° C. overnight. After a suitable number of washes with standard washing buffers, an optimal concentration of a biotinylated form of a composition/antigen of this invention dissolved in a conventional blocking buffer is applied to each well; a sample is added; and the assay proceeds as above.

Another useful assay format is a lateral flow format. Antibody to human or animal antibody or staph A or G protein antibodies is labelled with a signal generator or reporter (i.e. colloidal gold) that is dried and placed on a glass fiber pad (sample application pad). The diagnostic peptide is immobilized on membrane, such as a PVDF (polyvinylidene fluoride) membrane (e.g. an Immobilon membrane (Millipore)) or a nitrocellulose membrane. When a solution of sample (blood, serum, etc) is applied to the sample application pad, it dissolves the colloidal gold labelled reporter and this binds to all antibodies in the sample. This mixture is transported into the next membrane (PVDF or nitrocellulose containing the diagnostic peptide) by capillary action. If antibodies against the diagnostic peptide are present, they bind to the diagnostic peptide striped on the membrane generating a signal. An additional antibody specific to the colloidal gold labelled antibody (such as goat anti-mouse IgG) is used to produce a control signal.

It should be understood by the one of skill in the art that any number of conventional protein assay formats, particularly immunoassay formats, may be designed to utilize the isolated peptides of this invention for the detection of a HIV-1 infection in a subject. This invention is thus not limited by the selection of the particular assay format, and is believed to encompass assay formats that are known to those of skill in the art.

Reagents for ELISA or other assays according to this invention can be provided in the form of kits. Such kits are useful for diagnosing infection with a HIV-1 virus, using a sample from a subject (e.g. a human or other animal). Such a diagnostic kit can contain an peptide of the invention (and, if desired, additional peptides as discussed above) and, optionally, a system for (means enabling) detection of a peptide of the invention bound to an antibody directed against a peptide of formula (I), and/or a surface to which the peptide can be bound. In one embodiment, a kit contains a mixture of suitable peptides or means for preparing such mixtures, and/or reagents for detecting peptide-antibody complexes.

The kit can include microtiter plates to which the peptide(s) of the invention have been pre-adsorbed, another appropriate assay device, various diluents and buffers, labelled conjugates or other agents for the detection of specifically bound antigens or antibodies, and other signal-generating reagents, such as enzyme substrates, cofactors and chromogens. Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex. Such kits provide a convenient, efficient way for a clinical laboratory to diagnose infection by a HIV-1 virus.

In some embodiments, the diagnostic methods and kits described herein may be used for detecting generally the presence of anti-HIV-antibodies in a sample previously collected from an individual. In some other embodiments, the diagnostic methods and kits described herein may be used for determining the identity of the HIV-1 virus subfamily that has infected the individual who is currently tested.

In some embodiments, diagnostic methods and kits described herein make use of only one peptide selected from the peptides belonging to the family of peptides of formula (I).

In other embodiments, diagnostic methods and kits described herein make use of a plurality of peptides selected from the peptides belonging to the family of peptides of formula (I).

Illustratively, embodiments of diagnostic methods and kits described herein make use of a plurality of peptides of formula (I) selected from the group consisting of:

```
PWNASASNKSLDDIW  (SEQ ID No 12),

PWNASWANKSLDDIW  (SEQ ID No 13),

PWNASWSAKSLDDIW  (SEQ ID No 14),
and

PWNASWSNKALDDIW  (SEQ ID No 15),
```

The present invention is further illustrated by, without being limited to, the examples hereafter.

EXAMPLES

Material and Methods of the Examples

1. Preparation of Virus

Mutants were prepared from plasmid pNL4.3 using the QuickChange II XL Site-directed mutagenesis kit (Stratagene) with subsequent verification by DNA sequencing.

Wild type and Alanine-mutated 3S/gp41 pNL4.3 plasmids were transfected by lipofectamine (Invitrogen) into 293T cells in Optima medium. Forty-eight hr post-transfection, cell-free supernatant was harvested and the concentration of the HIV major core protein p24 using the Vidas Ag p24 II kit (Biomerieux). Virus supernatants are preserved at −80° C.

2. Peptides and Antibodies

Purified unconjugated and KLH-conjugated wild type and alanine-mutated 3S/gp41 synthetic peptides (FIG. 1) were purchased from Covalabs (Villeurbanne, France). Mice were twice IV-injected with about 2-weeks interval between each injection of 20 mg of KLH-linked peptide, in the presence of incomplete Freund's adjuvant. The sera were titrated by enzyme-linked immunosorbent assay (ELISA) by using Maxisorp plates (Nunc) coated overnight at 4° C. with 100 ng of wild type or alanine-mutated 3S/gp41 peptides, as described (Vieillard et al AIDS 2006).

3. Purification of Primary Healthy CD4+ T Cells

Leukocytes from whole-blood samples from healthy donors were obtained by buffy-coat centrifugation from the "Etablissement Francais du sang" (Hôpital Pitié-Salpêtriêre, Paris, France). CD4+ T cells were purified with CD4 magnetic microbeads (Miltenyi). Flow cytometric analysis demonstrated a purity more than 95% CD4 cells. Cells were activated for 3 days with 1 μg/ml PHA-L (Murex) in RPMI-1640 Glutamax medium (Invitrogen) supplemented with 10% fetal calf serum (FCS), and then cultured with 100 IU/ml Proleukin-2 (Chiron), added every 3 days.

4. Infection Assay

Purified activated CD4+ T, MT2 and Jurkat cells ($10^7$ cells) were incubated with 100 ng of p24 antigen equivalents, for 17 h and 2 h at 37° C., respectively. Cells were then washed twice in PBS/EDTA and resuspended at $10^6$/mL. Virus production was monitored every 2 days post-infection by ELISA to measure the concentration of p24 with the Vidas Ag p24 II kit (Biomerieux). Syncytium formation on infected MT2 cells was assessed after 96 h by standard phase contrast microscopy.

5. Single-Round HIV-1 Infectivity Assay

Hela P4C5, kindly gift by A. Morris and O. Schwartz (Pasteur Institute Paris, France) were co-transfected by CD4⁻ and CCR5⁺, and contained an integrated copy of HIV-1 long terminal repeat (LTR) linked to a luciferase and β-galactosidase gene (Amara et al J. Exp. Med. 1997). Cells were seeded one day before and infected with 4 ng p24/ml of wild type or alanine-mutated 3S/gp41 NL4.3 viruses. At 48 h post-infection, the β-galactosidase activity was measured in Hela-P4C5 cell-lysates using the CPRG Beta-Galactosidase Kit (OZ biosciences).

6. Neutralization Assays

Polyclonal IgG fraction from mice anti-sera were isolated using Nab Protein A/G Spin kit, and then desalted using Zeba spin desalting columns, both from Thermo Scientific, according to the manufacturer's instructions. Immunoglobulin fractions were concentrated with Centricon Centrifugal Filter Units (Millipore), and then quantified using BCA protein assay kit (Thermo Scientific). Purified Abs were tested at starting concentrations of 20 μg/ml followed by five 2-fold dilutions.

Human anti-WT or anti-W614A 3S/gp41 Abs were purified by immunoprecipitation from heat inactivated plasma of HIV-infected patient using the Pierce Direct IP kit by direct immunobilizing synthetic peptide onto an amine-reactive agarose support. Purified Abs were then dialysis against PBS (Silde-A-Lyser Dialysis cassette, Pierce), and quantified. The purified Ab were tested at starting concentrations of 2 μg/ml followed by five 2-fold dilutions.

Two assays using infectious viruses were performed to test neutralization of the purified Abs (Fenyö et la PLoS one 2009):

(1) To compare the potency (concentrations required to achieve 50% [IC50] and 90% [IC90] inhibition) of Abs, we first used a CD4+ T cells-p24 assay. Infectious replication-conpetent viruses ($200TCID_{50}$) were incubated with various concentration of Ig for 30 min followed by addition of PHA-activated purified CD4+ T cells, in the presence of IL2. Seven days after initiation of the infection duplicate samples were harvested for measurement of p24 (Vidas Ag p24 II kit, Biomerieux).

(2) To evaluate the possibility for differential neutralization activity of the various purified Ab, we measured their ability to inhibit HIV-1 entry from different X4 (NL4.3, BRU, NDK) and R5 (JR-CSF, YU-2) strains, or ROD HIV-2, using Hela-P4C5 and/or TZM-bl cells (NIH AIDS Research and Reference Reagent Program), kindly provided from Clarisse Berlioz-Torrent (Institut Cochin, Paris, France). Infectious replication-competent viruses ($200TCID_{50}$) were incubated with various concentrations of Ig for 30 min, followed by addition of Hela P4C5 cells. At 48 h post-infection, the β-galactosidase activity is measured in Hela-P4C5 lysates using the CPRG Beta-Galactosidase Kit (OZ biosciences), and Luciferase activity is measured in TZM-bl lyzates using the Britelite Plus Reagent (Perkin Elmer). A cut-off value of 2.5-times background was applied to determine positive values in TCID assays. Data were expressed in $TCID_{50}$ and $TCID_{95}$.

7. Flow Cytometry

FACS analysis was performed on purified CD4+ T cells in the presence of viable or heat-inactivated virus for 17 h, or treated with 3S/gp41 peptides for 4 h at 37° C. Samples were incubated with 1 μg of each antibody: anti-NKp44L, or with fusion proteins (NKp30-Ig, NKp44-Ig, or NKp46-Ig) for 2 h at 4° C. in the presence of PBS/BSA1%. Cells were then washed in PBS/BSA1% and incubated for 30 min at 4° C. with specific secondary antibodies (diluted 1:100 in PBS/BSA1%), and fmally stained directly with anti-CD4 mAb and fixed using BD CellFix solution (BD Bioscience), as described (Vieillard et al PNAS 2005). At least 10,000 events of CD4$^+$ cells were detected on a FACSCanto (BD Biosciences) or Navios (Coulter).

8. Degranulation Assay

Uninfected or CD4$^+$ T cells infected with the wild type or alanine-mutated 3 S/gp41 NL4.3 viruses were resuspended at a 1:1 ratio in the presence of autologous IL2-activated autologous PBMC, and anti-CD107a mAb (H4A3; Becton Dickinson). After 1 h incubation, 3 mM monensin was added for an additional 3 h of incubation, as previously described (Béziat et al PLoS One 2010). NK cells were stained with anti-CD3, anti-CD56, and anti-NKp44 mAb, and analyzed on a FACSCanto (BD Biosciences) or Navios (Coulter). At least 5,000 CD3$^-$CD56$^+$ events were analyzed.

Example 1: Integrity of the 3S/gp41 of CD4 for Infection of CD4$^+$ T Cells

Figure 2B:
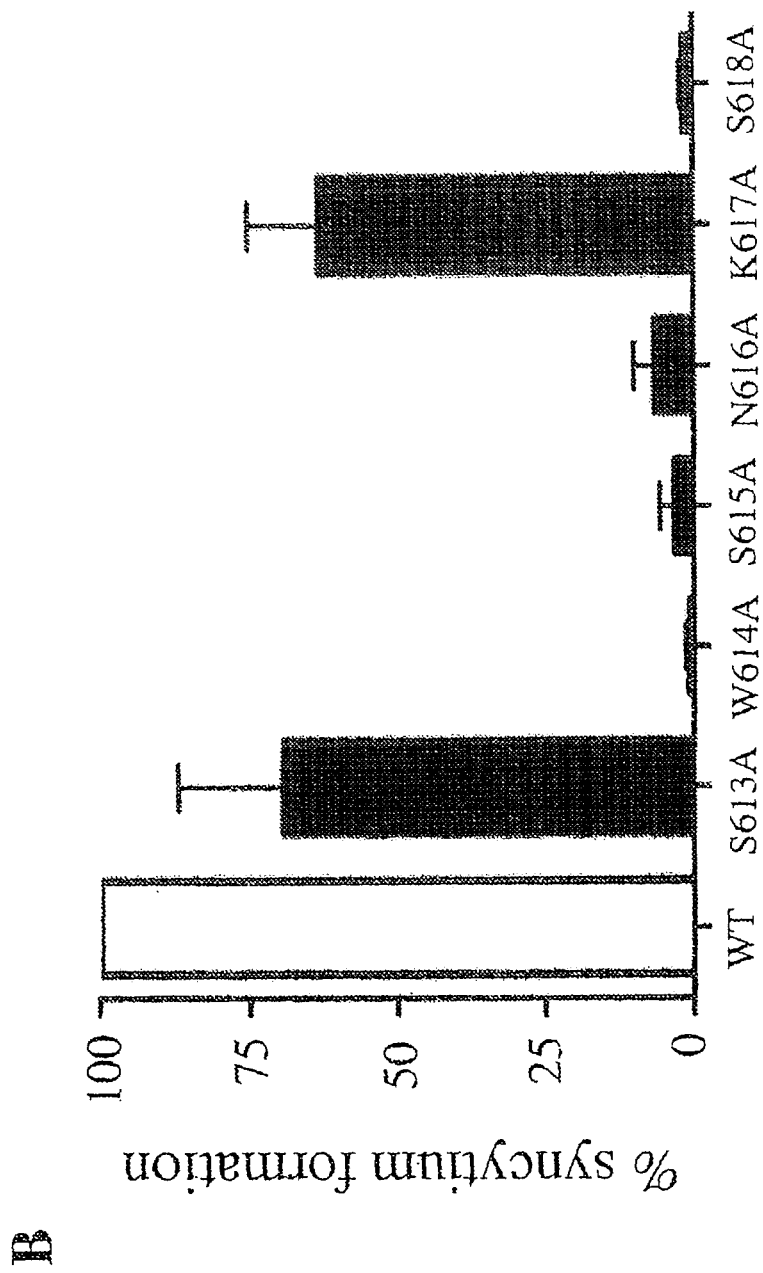

To delineate the role of the 3S/gp41 motif in the virus life cycle, single point substitutions were individually introduced at residues ranged between position S613 and S618 inside the 3S motif of the gp41 protein from the NL4.3 HIV-1 strain. To examine whether these single substitutions exert an effect on virus infectivity, MT-2 cells were challenged with 100 ng p24 equivalent antigen from each virus preparation. FIG. 2A shows that the effects of substitutions of the 3S/gp41 motif are ranged from the near complete abolishment of viral production to no effect with respect to virus expressing wild-type motif. Indeed, S613A mutated-virus preserved his complete capacity to infected MT-2, while K617A in still 66±10% of the level observed to the wild-type, and the others mutants less than 22%. It seems that W614A and S618A mutants are incapables to establish an infection in MT-2 cells (FIG. 2A). These data were confirmed with the capacity of these mutants to perform syncytium formation, with the complete absence of these giant cell-structures in MT-2 cells infected with either W614A and S618A mutated viruses, as compared to the wild-type (FIG. 2B). These data suggest that both positions, W614 and S618, of the 3S/gp41 motif, may play a critical role during viral infection.

Figure 2C:
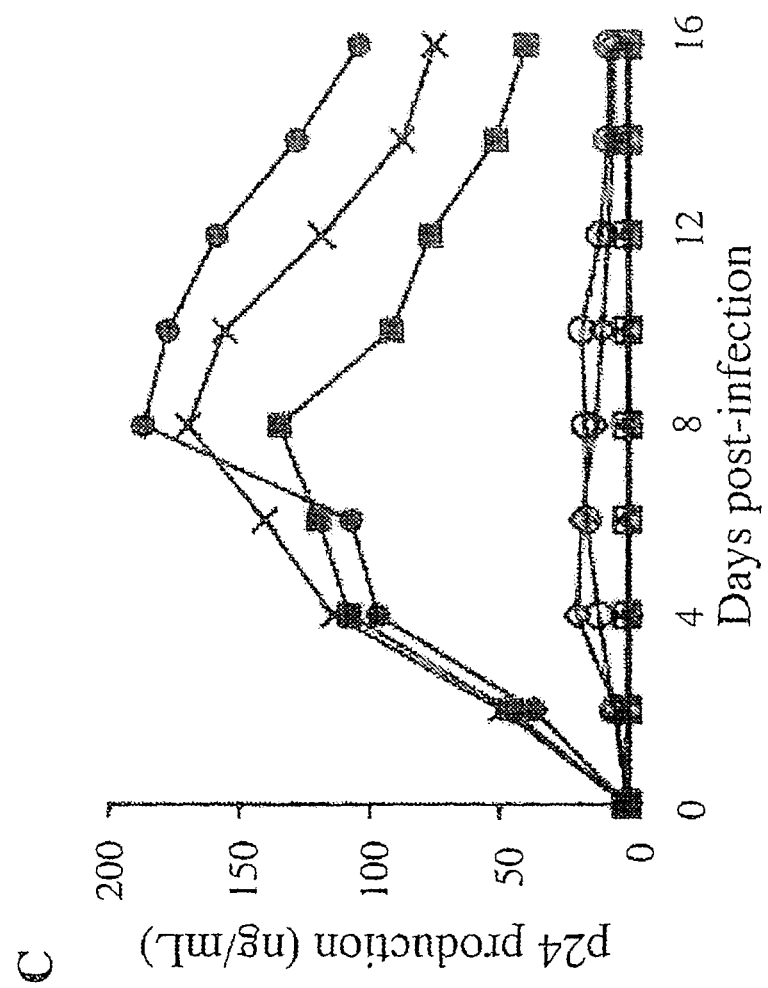

Kinetic studies of infection in purified CD4$^+$ T cells revealed that wild-type and the S613A and K617A mutants showed very productive viral replication (up to 187 pg/ml p24) with a peak of p24 production 8 days after infection (FIG. 2C). In contrast, whatever the time period, the infectious level of S615A and N616A mutates-viruses remains very lower, with 13.5 and 17.3 pg/ml, at the peak of viral load, respectively, and remains undetectable with W614A and S618A (FIG. 2C). Similar results were observed in the presence of infected Jurkat cells (data not shown).

Figure 2D:
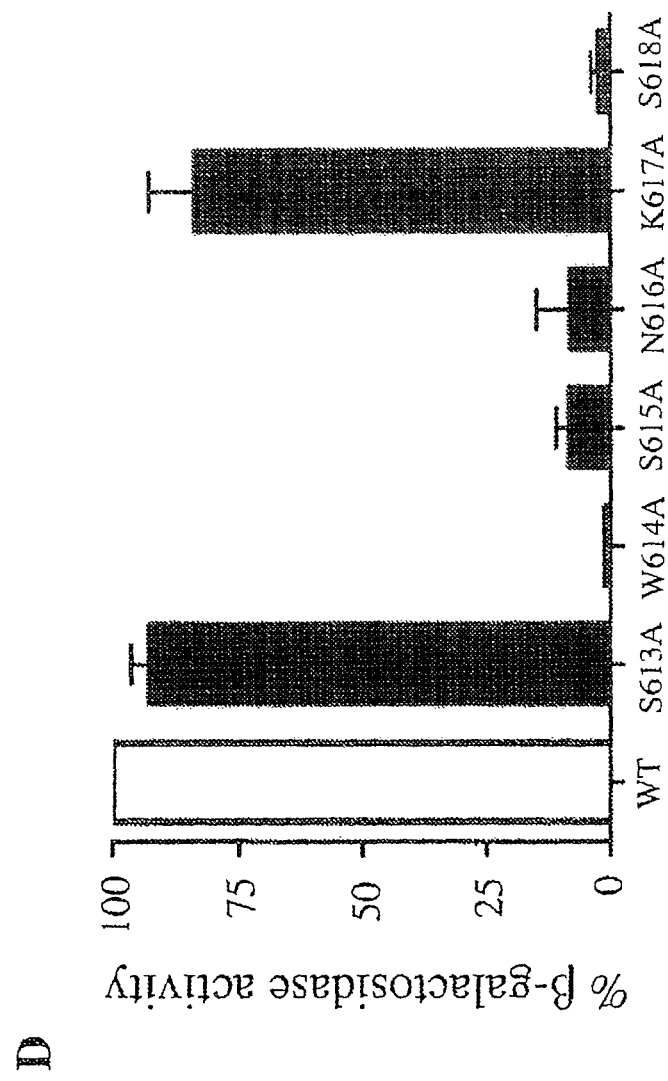

We next sought to determine which step of the viral cycle was affected by mutation into the 3S/gp41 motif. In order to evaluate the infectivity of the 3S/gp41 mutants, viral supernatants from transfected 293T cells were tested on Hela P4C5 indicator cells, a Hela derivative cell-line carrying an HIV-LTR Lac-Z cassette activated by Tat upon HIV-1 infection (Amara et al J Exp Med 1997). As FIG. 2D show, both S613A and K617A mutants are preserved the capacity to infected cells, similarly to the wild-type. By contrast, in the presence of S615A, N616A, and S618A mutants, the level of infectivity is at least 10-fold lower than with the wild-type, and completely undetectable with the W614A mutant. This suggests that peculiar substitutions at specific positions in the 3S/gp41 motif inhibit virus-entry in CD4$^+$ T cells.

Figure 3A:
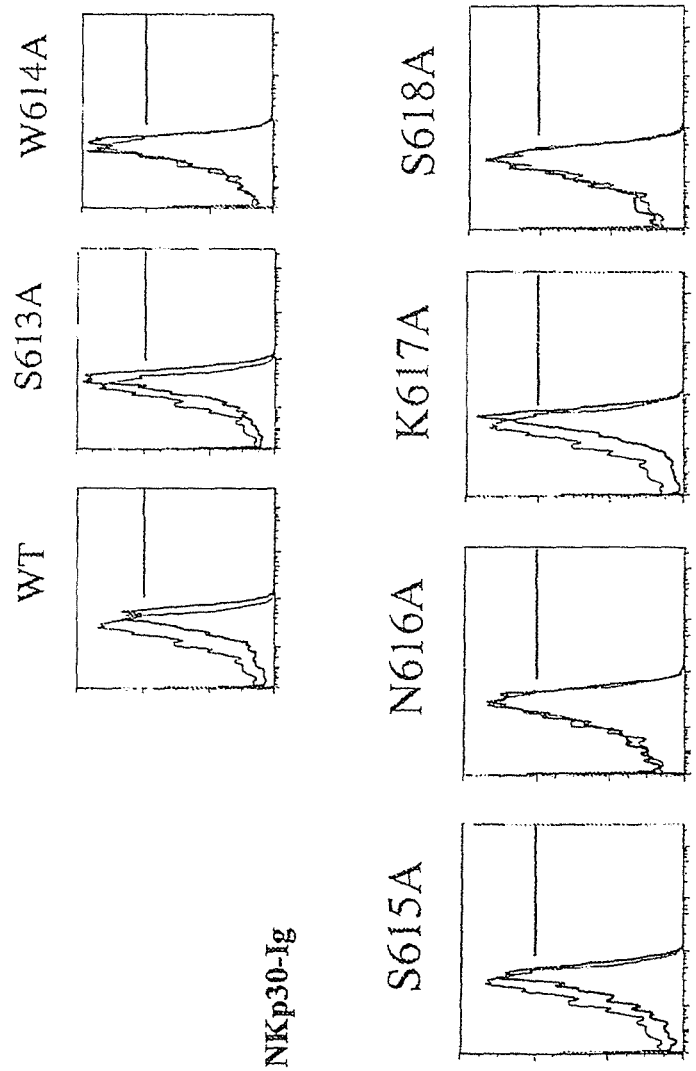
Figure 3A:
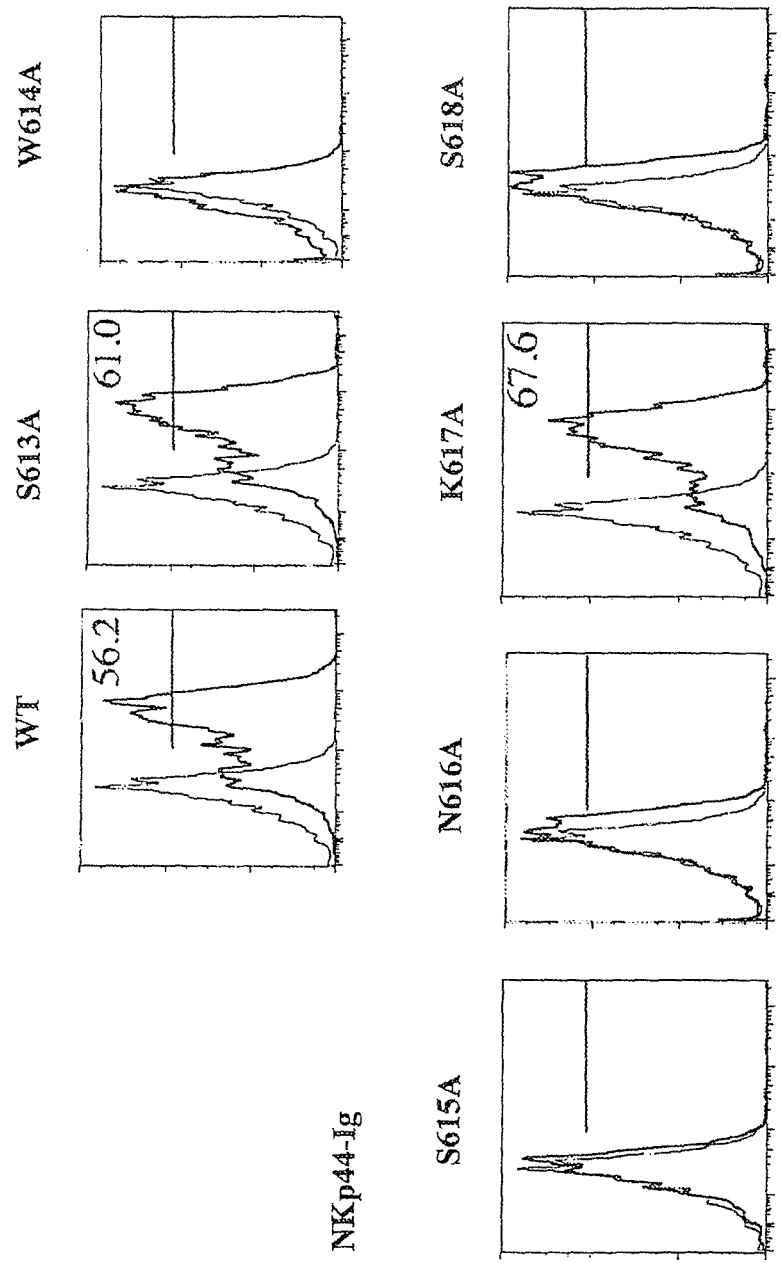
Figure 3A:
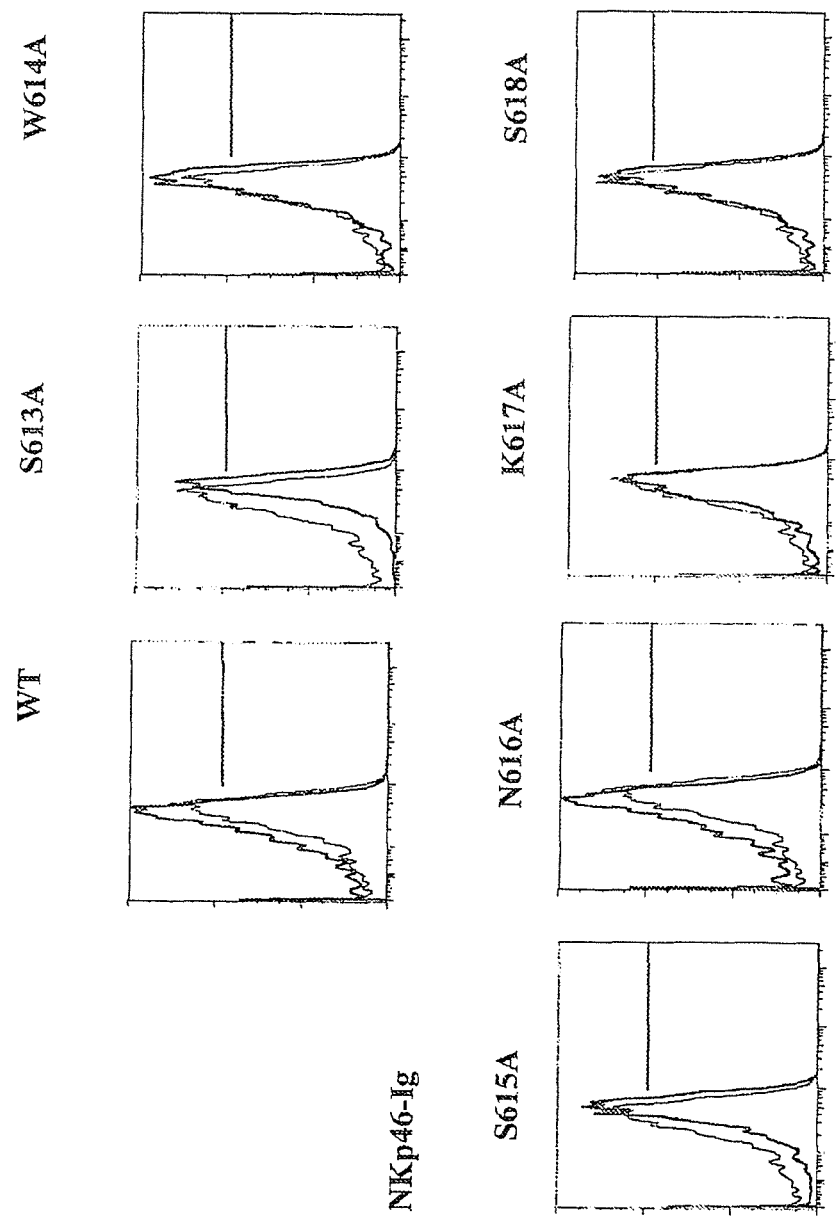
Figure 3B:
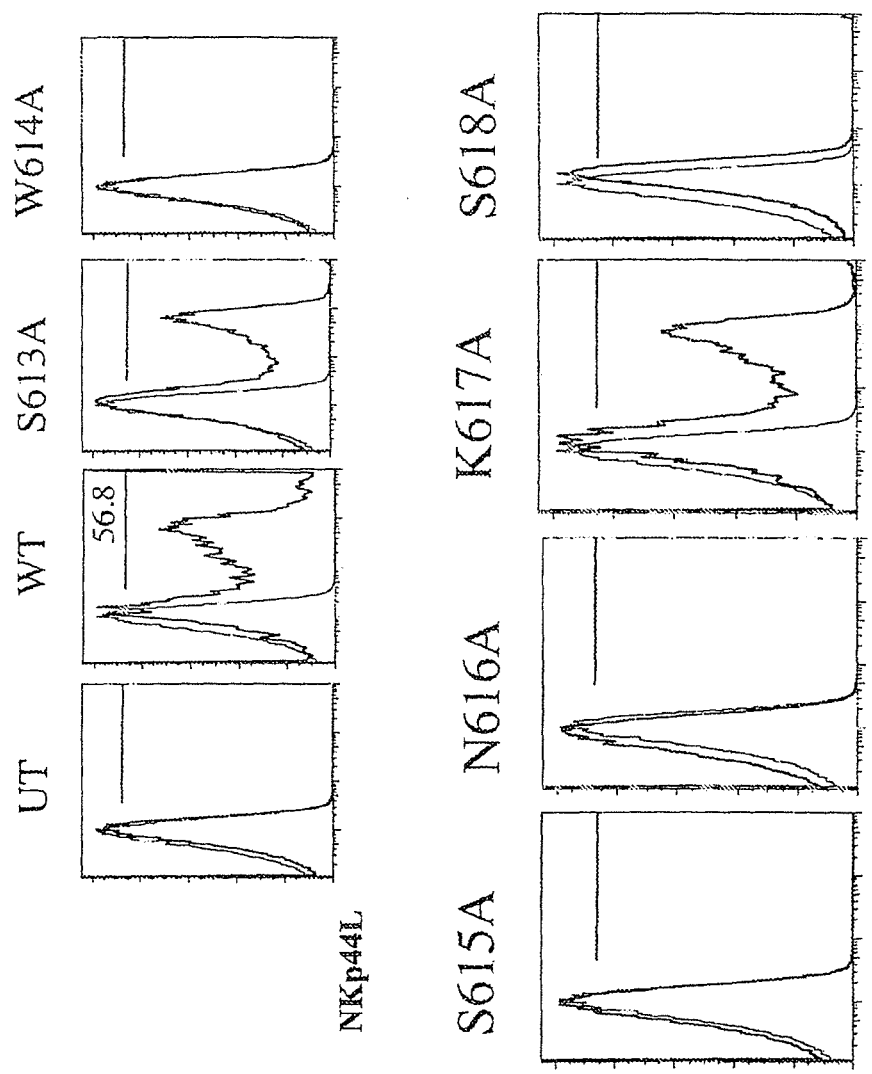

Example 2: Point-Mutations in the 3S/gp41 Motif Abolish Expression of NKp44L As previously shown by others and us, HIV-1 infection induce expression of certain NKR ligands, including NKp44L (Vieillard et al 2005; Ward et al 2007). We wanted to determine whether virus containing 3S/gp41 substitutions are also capable to induce expression of NKp44L on purified CD4$^+$ T cells. After infection with wild-type virus, high frequency of cells expressed NKp44L (56.2%). Similar results were obtained with CD4$^+$ T cells infected with the S613A or K617A mutants, with 61.0 and 67.6% of cells expressing NKp44L, respectively. More intriguingly, no expression was detected with the other mutants; W614A, S615A, N616A, and S618A. Consistently with previous data (Vieillard et al 2005; Ward et al 2007) expression of NKp30 and NKp46 ligands were not induced on cells infected by either wild-type, or alanine-mutated 3S/gp41 viruses, whatever the position of the substitution (FIG. 3A).

We next investigated the possibility that NKp44L expression is differentially regulated in absence of infectious particles. Thus, in the presence of heat-inactivated virus (FIG. 6A), or after stimulation with synthetic 3S-peptides including the various alanine-substitutions in the 3S/gp41 motif (FIG. 3B), similar results of those obtained with competent-virus while respecting their specific residue substitution. Indeed, expression of NKp44L is only induced in the presence of S613A, and K617A mutated-elements, at a level closed to this observed with the wild-type, whereas, the other non-infectious particles or peptides mutants are not able to induce NKp44L.

Figure 3C:
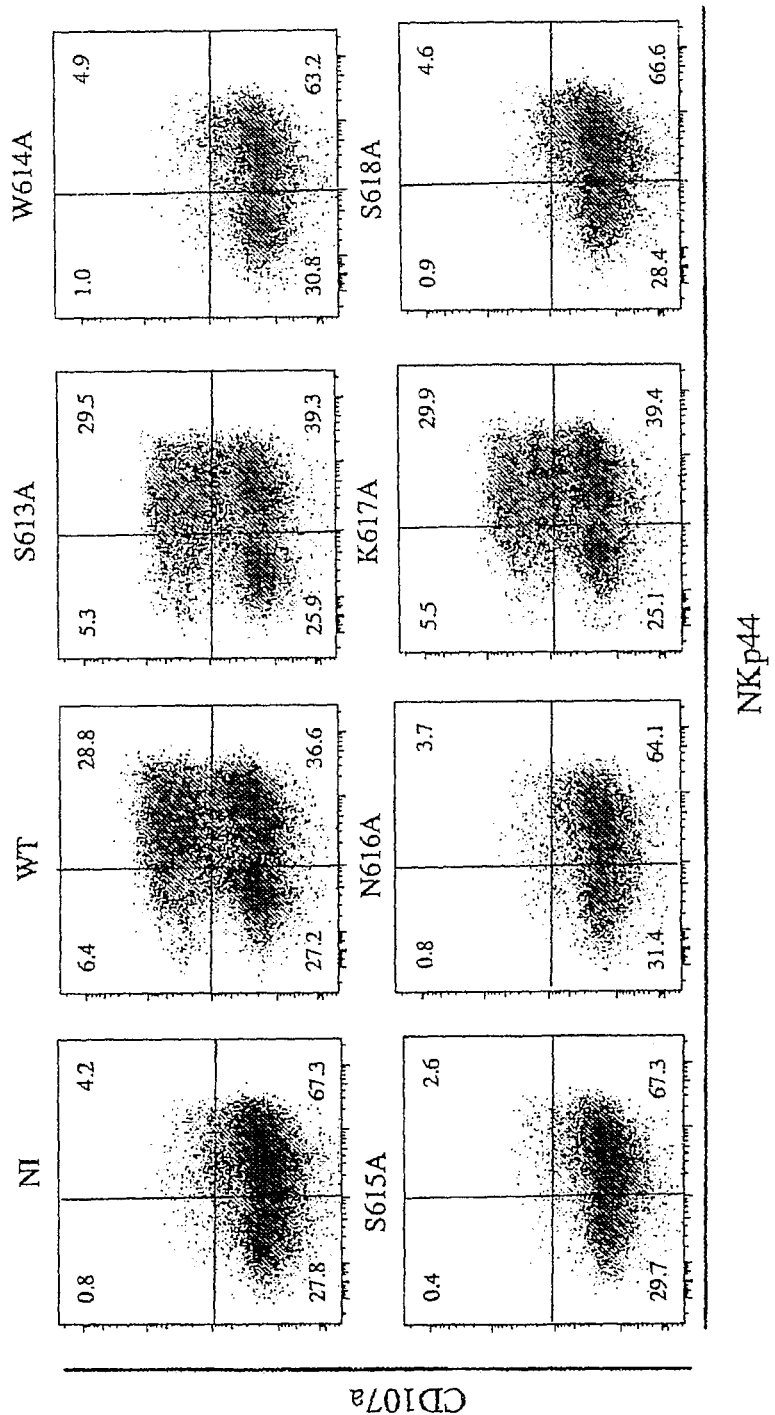
Figure 3D:
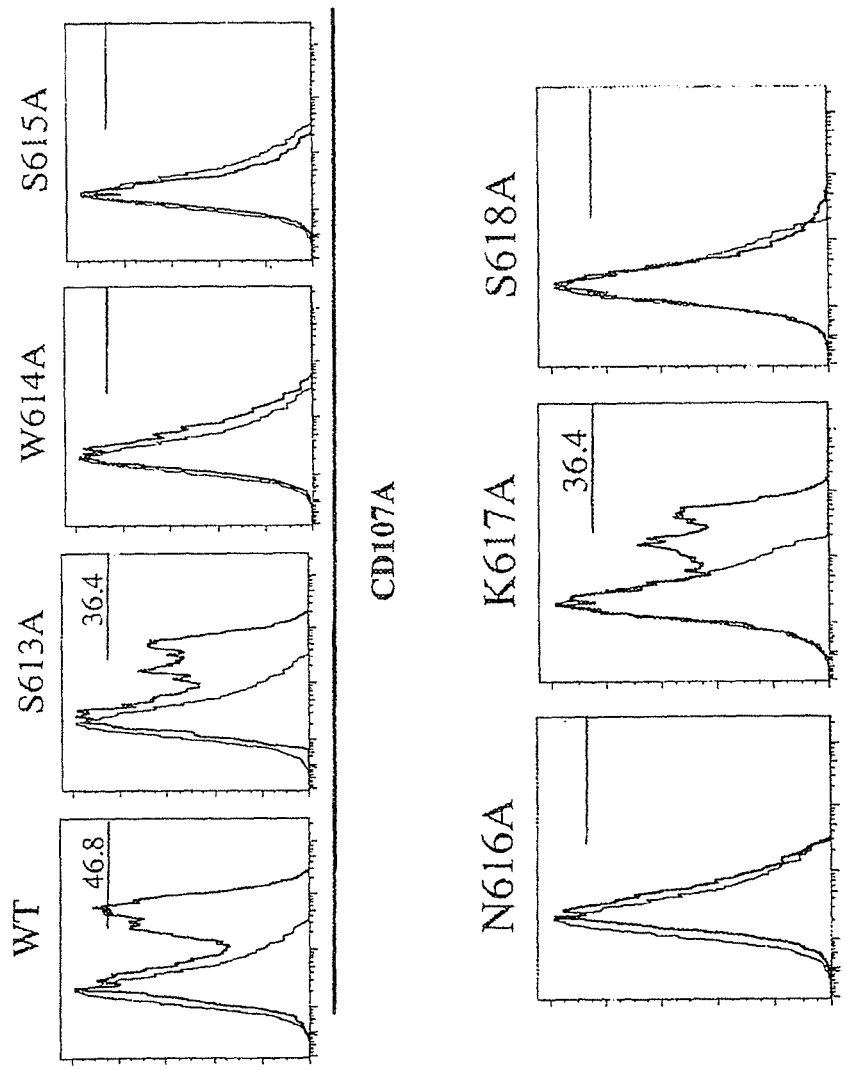
Figure 4A:
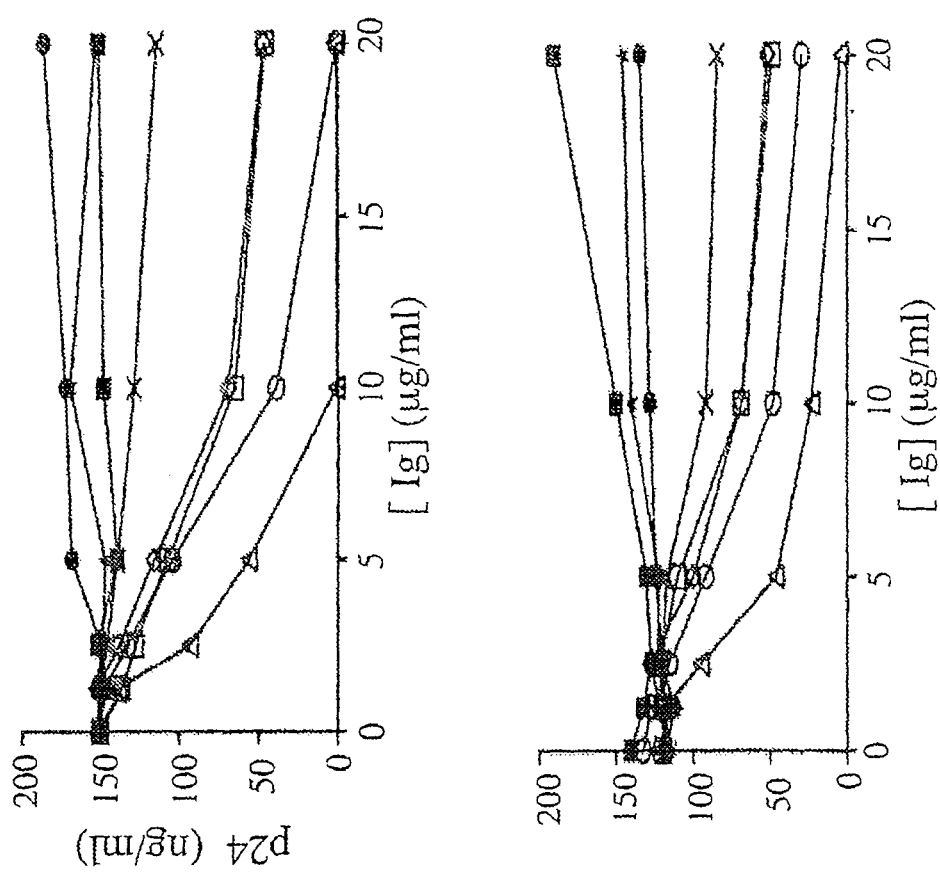
Figure 4B:
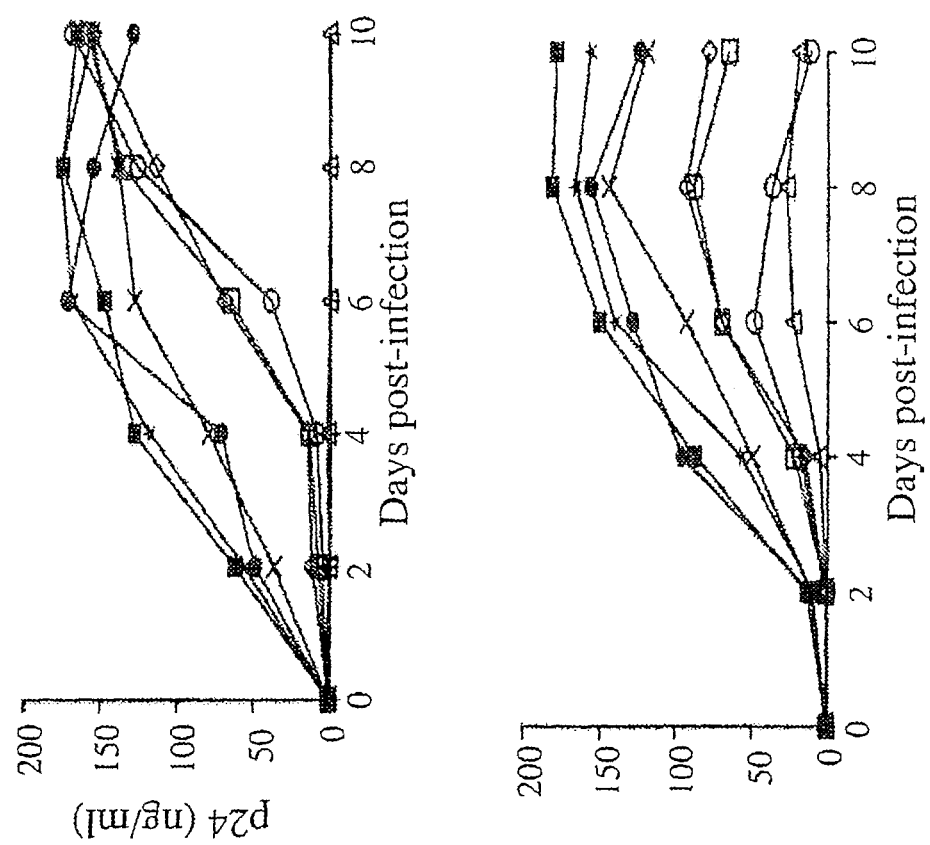
Figure 4C:
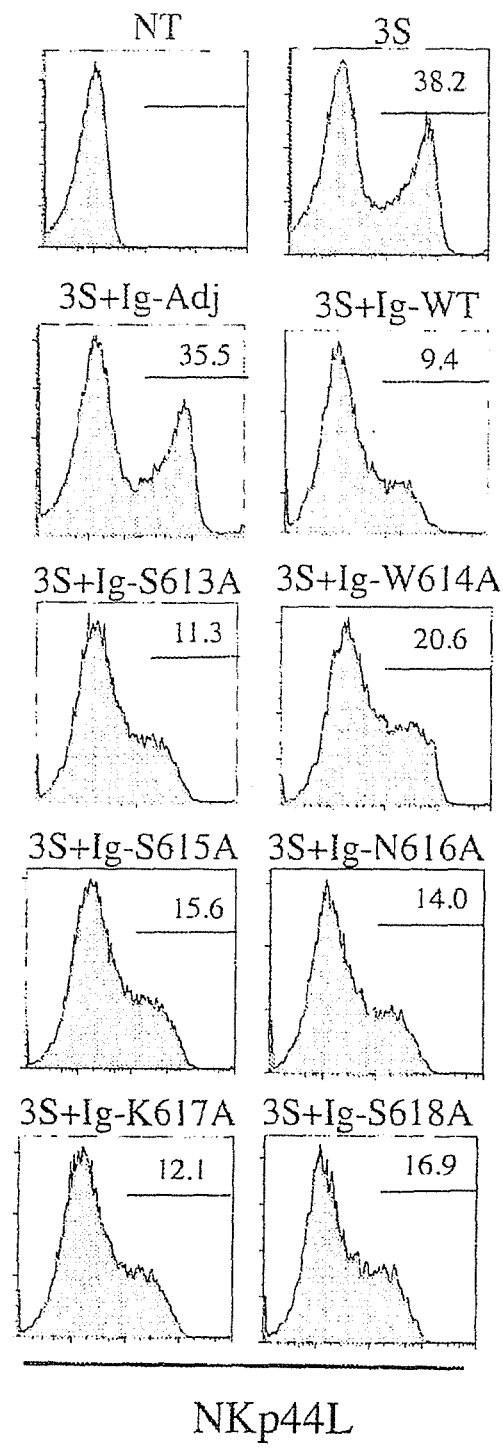
Figure 4D:
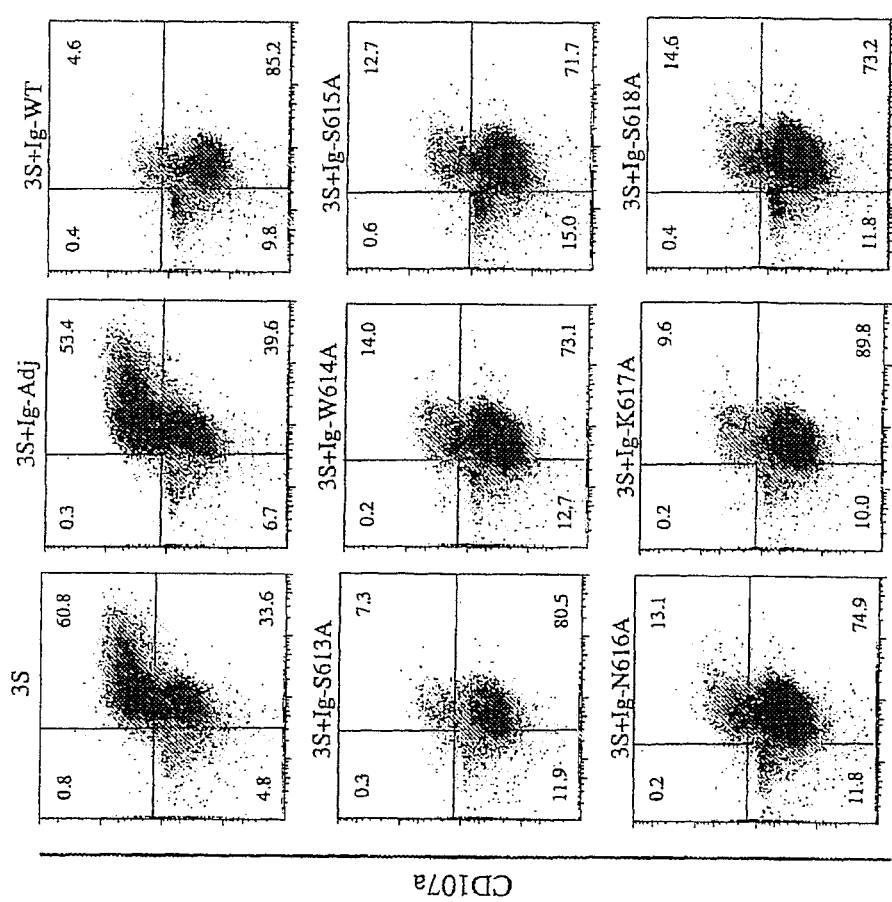

Example 3: Modulation of the Degranulation of NK Cells in the Presence Autologous CD4$^+$ T Cells Infected by 3S/gp41 Viral Mutants Because we found NKp44L on CD4$^+$ T cells infected with NL4.3 virus containing certain 3S/gp41 mutations (FIG. 2A), we investigated the possibility that target cells expressing this ligand are more sensitive to NK cytotoxicity. Purified CD4$^+$ T cells infected either with wild-type or the various mutated viruses were incubated with autologous IL2-activated NK cells to determined their degranulation capacities. FIG. 3C shows that, high expression of CD107a on NKp44$^+$ NK cells, was detected in presence of wild-type virus (28.8%), or the S613A (29.5%), and K617A (29.9%) mutants, as compared to non-infected cells (4.2%), in line with data showing high expression of NKp44L on the CD4$^-$ target T cells (FIG. 3A). By contrast with the other mutants, for which, we do not observed induction of NKp44L on CD4$^+$ T cells, the level of degranulation remains nearly closed to this obtained with non-infected cells (FIG. 3C). Similar results were obtained in the presence of heat-inactivated viral particles (FIG. 6B), and synthetic peptides (FIG. 4D).

Altogether, these results strongly suggest that substitutions of peculiar residues within the highly conserved 3S/gp41 motif induce major consequences concerning modulation of the NK-cell sensitivity of CD4$^+$ target cells.

Example 4: Elicitation of 3S-Like Broadly Neutralizing Antibodies in Mice

We therefore performed immunization of mice with wild-type and each Alanine-mutated 3S/gp41 peptides to generate specific antibodies. For all of them robust immune responses were seen against their specific 3S/gp41 sequence on free-peptide captured ELISA (Data not shown). Intriguingly, the magnitude of the sero-cross reactivity depends of the peptide component; the anti-serum interacting with each synthetic peptide in a manner directly proportional to their capacities to induce NKp44L expression. Thus, strong sero-cross reactivity was observed between wild-type and the S613A and K617A mutants, whereas, this effect is profoundly decreased with other mutants, consistently with putative conformational modifications induced by peculiar substitutions.

Figure 5A:
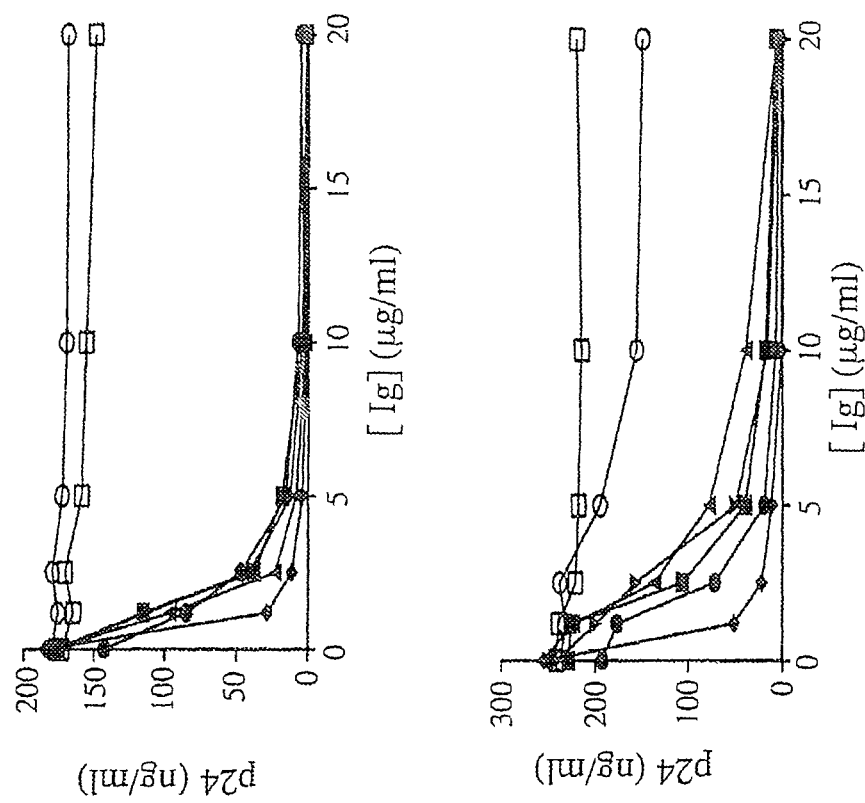
Figure 5B:
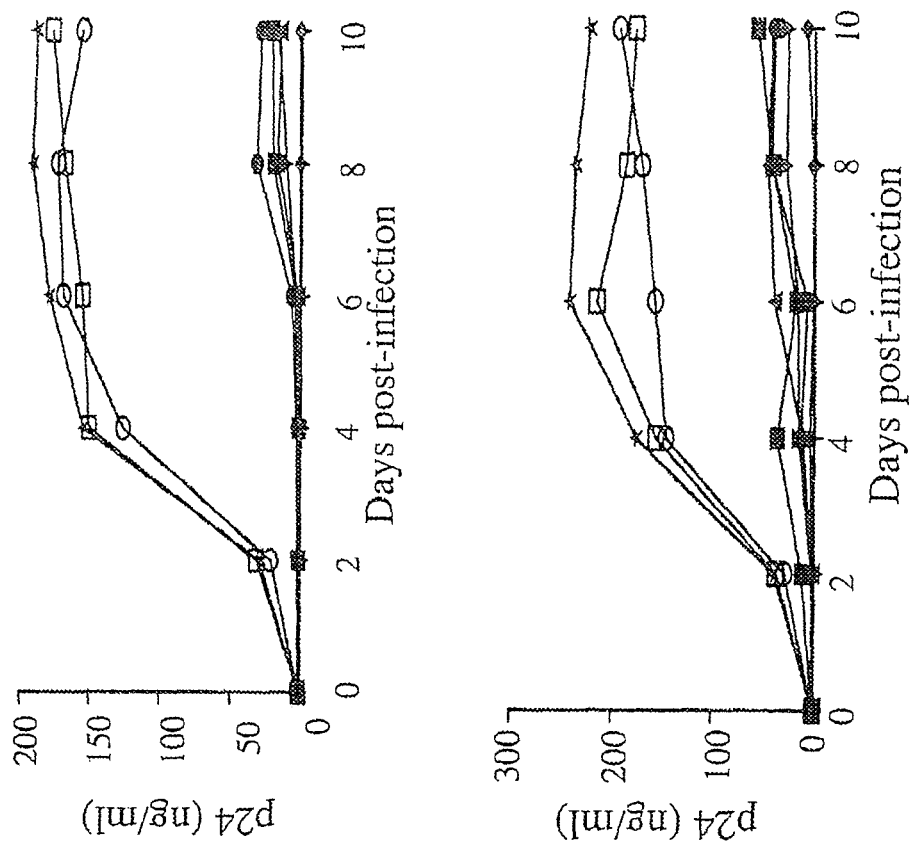
Figure 5C:
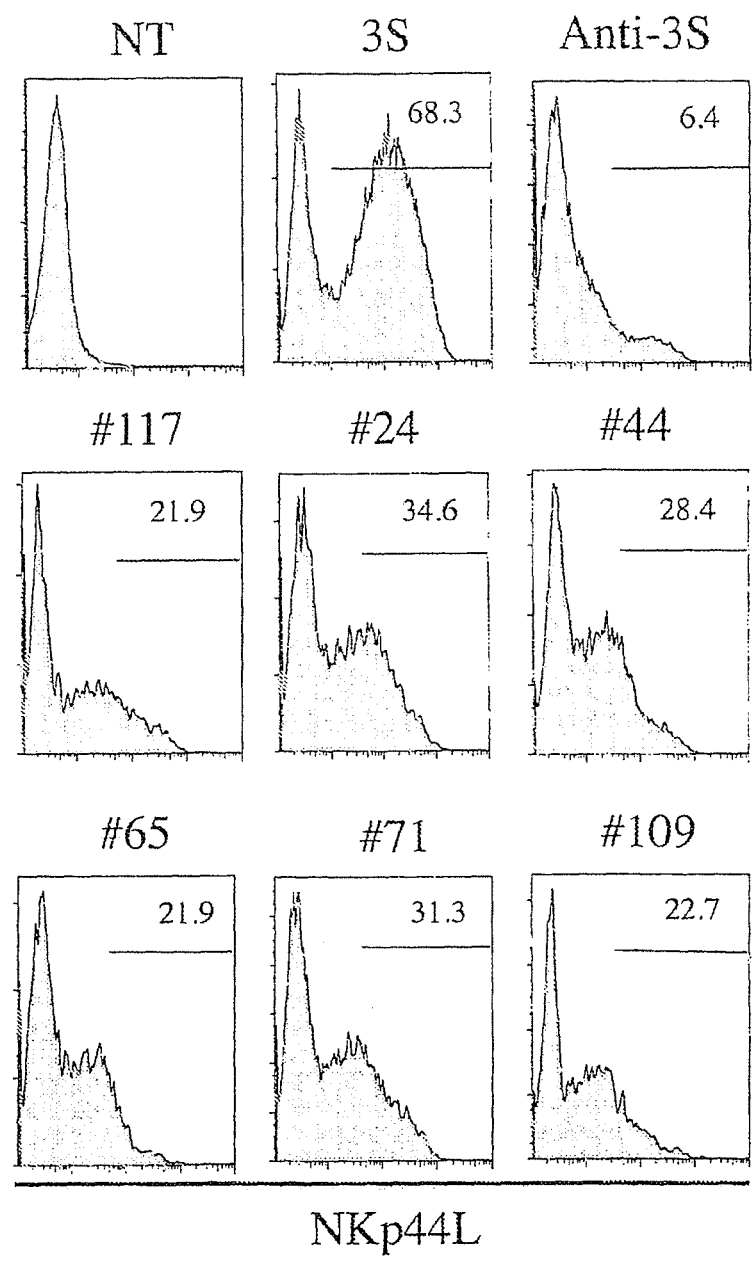
Figure 5D:
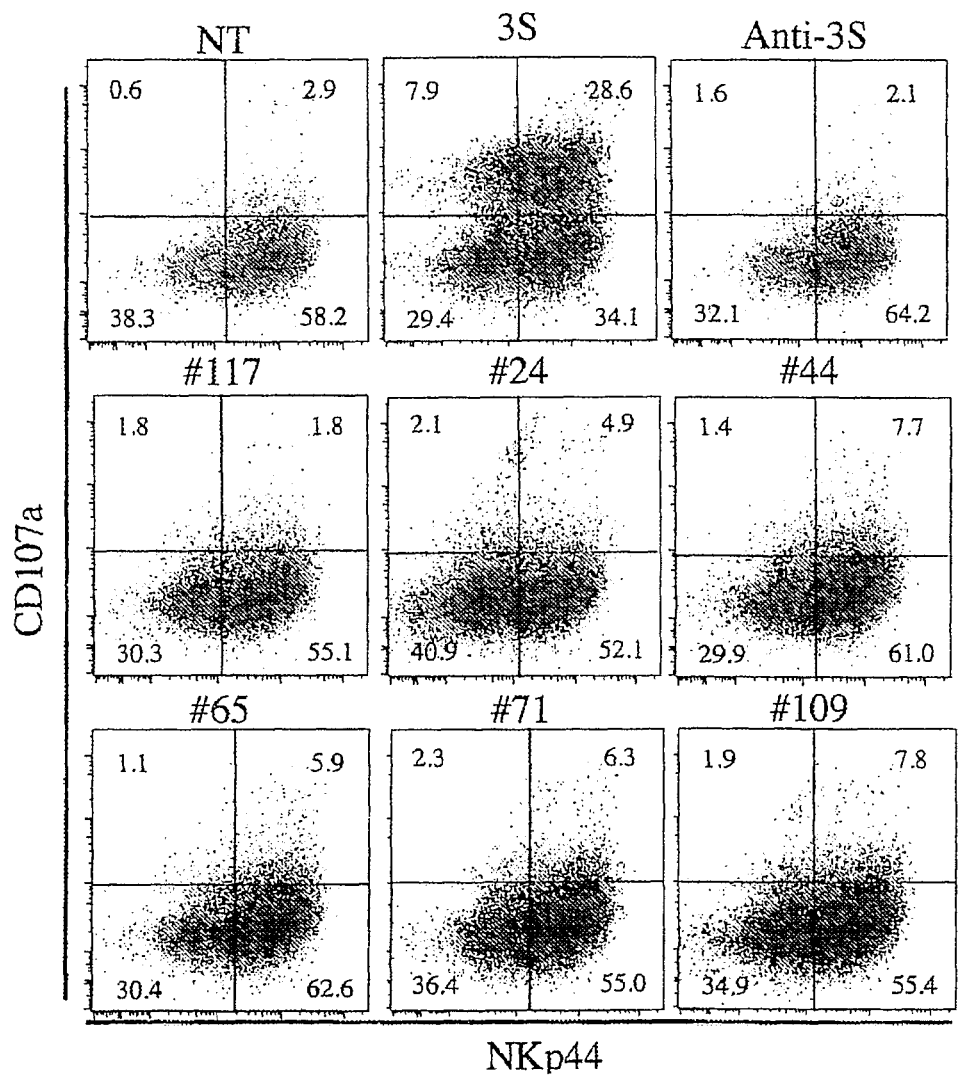

More importantly, whole immunoglobulins (Ig) were eluted off from each serum to assess their potency and breadth of neutralization on a cross-clade of R5 and X4 HIV-1 strains. Using different classical neutralizing assays using TZM-bl and Hela-P4C5 cells, we confirmed the absence of significant neutralizing activity of the anti-3S wild-type antibodies against HIV-1 (Tables 2 and 3), as previously described (Vieillard AIDS 2006). Similar results were observed in the presence of purifed Ig from the S613A and K617A immunized mutant mice. Surprisingly, robust and broadly neutralizing activity was detected for W614A, S615A, N616A and S618A mutants. Indeed, significant responses were elicited by each of these mutants against various X4 (NL4.3, BRU, and NDK), and R5 (JR-CSF and YU-2) HIV-1 strains with $IC_{50}$ valued ranged between 3.3 and 17.7 mg Ig/ml (Table 2). More importantly Ig from W614A are able to neutralize all X4 and R5 HIV-1 strains tested with an $IC_{95}$ ranged between 6.7 and 19.5 µg/mL in Hela-P4C5 cells (Table 2), and between 3.9 and 10.3 µg/mL in TZM-bl cells (Table 3), depending of the viruses. As expected, in the presence of an HIV-2 strain (ROD), no neutralizing activity was detected, whatever the condition (Table 3), in line with the specific deletion of the 3S/gp41 motif in HIV-2 strain sequences (Vieillard PNAS 2005).

To definitively confirm these data, we next determined the efficacy of viral neutralization by the detection of p24 production of purified $CD4^+$ T cells infected with NL4.3 or NDK HIV-1 strains. FIG. 4A confirms the absence of neutralizing activity against NL4.3 by Ig from WT, or S613A and K617A mutants, whatever their concentration. By contrast, significant decreased of p24 production was observed in the presence of Ig from W614A, S615A, N616A and S618A mutants. Interestingly, at a concentration superior to 10 μg/ml Ig from W614A, p24 antigen remains undetectable. Similar results were observed after infection with NDK (FIG. 4A). Furthermore, kinetic study revealed that production of p24 is completely abolished with 10 μg/ml Ig from W614A mutant whatever the time post-infection, and significantly delayed with Ig from S615A, N616A and S618A mutants, compared to wild type and the S613A and K617A mutants (FIG. 4B). Altogether, these data strongly support that substitution at specific positions into the highly conserved 3S/gp41 motif elicited production of broadly neutralizing activity in mice.

To further assess efficacy of NKp44L inhibition by Ig purified from alanine-3S/gp41 mutants, purified $CD4^+$ T cells from healthy donors were incubated with 3S/gp41 wild type peptide pre-treated with the purified Ig from the immunized mice. FIG. 4C shows that 3S-induced NKp44L expression is significantly decreased in the presence of Ig from 3S-WT (9.4%), as compared to control cells (35.5%), consistently with previous data with anti-3S wild type mAb (Vieillard et al PNAS 2005). More importantly, strong inhibition of NKp44L expression was also observed in the presence of alanine-3S/gp41 mutants, but slightly more pronounced with Ig from S613A and K617A, than W614A, S615A, N616A and S618A mutants (FIG. 4C). These results feet with degranulation data of IL-2-activated NK cells against autologous $CD4^+$ T Cells treated with 3S-peptide in the presence of Ab from WT or alanine-3S/gp41 mutants. Thus, degranulation was both inhibited at 91.4% in WT and 78.3±4.8% in alanine 3S/gp41 mutants, whatever the position of the substitution (FIG. 4D). This indicated that Ig generated from the 3S/gp41 peptide with specific substitutions acquire broadly neutralizing capacity while protecting that allowing the inhibition of NKp44L expression on $CD4^+$ T cells.

Example 5: Broadly NAbs Anti-W614A 3S Mutant in Plasma from HIV-1 Patients

It was recently demonstrated that broadly reactive Nab activities seems to develop over-time in HIV-infected patients. To obtain information on the frequency at which bNAb for substituted 3S/gp41 motif are elicited in HIV infection, we have analyzed neutralization activity in 106 plasma samples derived from HIV-1-infected patients with a variety of clinical characteristics. Of the 106 samples evaluated, 55/106 (52%) had detectable level of anti-3S-WT Ab, with values ranged between 15 and 325 AU/ml. A Spearman test reveals highly significant relationship between the amount of anti-3S Ab and the CD4 count ($p<0.0001$) (data not shown), as described (Vieillard et al AIDS 2006). Unexpectedly, antibodies specifically directed against the W614A mutated 3S/gp41 motif was detected in 5 to 106 plasmas (4.7%) by ELISA. For each of them, high level of Ab was detectable (ranged between 120 and 250 AU/ml). These specific antibodies were IgG isotypes (data not shown), and exclusively detected in patients with high CD4 count (822±89 CD4/$mm^3$), and undetectable viral load (below than 20 copies/ml) (Table 3). Of note these Ab specifically directed against the W614A mutated 3S/gp41 motif are not detectable in the plasma of healthy donors (data not shown), as well as Ab for the wild type motif (Vieillard et al AIDS 2006).

Plasma samples from these 5 peculiar patients were investigated, and neutralization levels, expressed as the reciprocal dilution of plasma, revealed cross-clade anti-HIV neutralizing activity for all of these plasma, with $IC_{50}>100$ for all of them, in the presence of X4 NL4.3 and R5 YU-2 viruses. Interestingly, the plasma from 1 of these patients (#109) neutralized at least 95% of HIV particles (Table 3). To confirm that neutralizing activity is associated with Ab specifically directed against the W614A 3S/gp41 mutated motif, Abs from the sera of the 5 HIV-infected patients were immuno-purified with the corresponding synthetic peptide. These eluted Abs show significant neutralizing activity with $IC_{50}$ values ranged between <0.2 and 1.9 μg/ml, or <0.2 and 1.9 μg/ml, in Hela-P4C5, and TZM-bl cells, respectively, for at least two different HIV-1 strains (Table 3). Strikingly, purified antibodies from 1 of these 5 patients (#109) show similar breadth of neutralizing activity against all X4 and R5 HIV-1 strains with $IC_{95}$ ranged between 0.6 and 1.9 μg/ml, whatever the neutralizing assay (Table 3). These data were confirmed by p24 production on purified $CD4^+$ T cells showing a robust neutralizing activity ranged between 0.2 and 1.0 μg/ml and 0.11 and 1.8 μg/ml after infection with NL4.3 and NDK, respectively (FIG. 5A). Furthermore, a kinetic study shows that the production of p24 in cell-free supernatant is very significantly decreased with 1 μg/ml immuno-purified Abs from HIV-1 infected patients, whatever the time post-infection, compared to controls (FIG. 5B).

Next, we wanted to determine the effect of NKp44L inhibition by these neutralizing bNAb, which specifically recognized the W614A 3S/gp41 mutated motif, purified from HIV-1 infected patients. FIG. 5C shows that all anti-W614A NAbs preserved their capacities to inhibit NKp44L, as compared to 3S-sensitized control cells; however, as compared to anti-3S/gp41 wild-type Ab, from mice or purified from HIV-1 patient (#117) the efficacy is slightly down-modulated. Indeed, 21.9% of cells expressed NKp44L in the presence of purified anti 3S-WT Ab, whereas 21.9 to 34.6% of cells remain NKp44L$^+$ after treatment with anti-W614A mutated 3S/gp41 bNAbs from HIV-1 patients. Importantly, co-cultured of autologous CD4$^+$ T cells, treated with wild type or anti-W614A 3S/gp41 purified Ab, with autologous IL2-activated NK cells revealed that CD107a expression is very significantly decreased or abolished, with values ranged between 1.8 and 7.8% of CD107a$^+$NKp44$^+$ NK cells, compared to 28.6% in NK cells co-cultured with 3 S-sensitized CD4$^+$ target T cells in absence of Ab (FIG. 5D). Together, these data reveal that elicitation of natural bNAb against a specific mutated form of the 3S/gp41 motif are present in some HIV-1 infected, possessing dichotomous effects, coupling both viral neutralization and inhibition CD4 depletion.

TABLE 1

Neutralization assay in Hela P4C5 cells

| Virus | 3S/gp41 mutant | Coreceptor specificity | IC$_{50}$ (µg/ml) | IC$_{95}$ (µg/ml) |
|---|---|---|---|---|
| NL4.3 | | X4 | >20 | >20 |
| | S613A | | >20 | >20 |
| | W614A | | 3.4 | 17.4 |
| | S615A | | 7.1 | >20 |
| | N616A | | 5.8 | 19.5 |
| | K617A | | >20 | >20 |
| | S618A | | 8.0 | >20 |
| BRU | | X4 | >20 | >20 |
| | S613A | | >20 | >20 |
| | W614A | | 3.8 | 6.7 |
| | S615A | | 8.1 | >20 |
| | N616A | | 3.3 | 6.0 |
| | K617A | | >20 | >20 |
| | S618A | | 8.6 | >20 |
| NDK | | X4 | >20 | >20 |
| | S613A | | >20 | >20 |
| | W614A | | 3.3 | 12.9 |

TABLE 1-continued

Neutralization assay in Hela P4C5 cells

| Virus | 3S/gp41 mutant | Coreceptor specificity | IC$_{50}$ (µg/ml) | IC$_{95}$ (µg/ml) |
|---|---|---|---|---|
| | S615A | | 5.9 | >20 |
| | N616A | | 4.2 | >20 |
| | K617A | | >20 | >20 |
| | S618A | | 8.9 | >20 |
| JR-CSF | | R5 | 18.1 | >20 |
| | S613A | | >20 | >20 |
| | W614A | | 6.1 | 19.5 |
| | S615A | | 15.7 | >20 |
| | N616A | | 5.6 | >20 |
| | K617A | | >20 | >20 |
| | S618A | | 11.0 | >20 |
| YU-2 | | R5 | >20 | >20 |
| | S613A | | >20 | >20 |
| | W614A | | 10.3 | 19.5 |
| | S615A | | 17.7 | >20 |
| | N616A | | 8.3 | >20 |
| | K617A | | >20 | >20 |
| | S618A | | 16.8 | >20 |

TABLE 2

Neutralization assay in TZM-bl cells

| Virus | 3S/gp41 mutant | Coreceptor specificity | IC$_{50}$ (µg/ml) | IC$_{95}$ (µg/ml) |
|---|---|---|---|---|
| NL4.3 | | X4 | >20 | >20 |
| | S613A | | >20 | >20 |
| | W614A | | 5.4 | 17.4 |
| BRU | | X4 | >20 | >20 |
| | S613A | | >20 | >20 |
| | W614A | | 3.9 | 11.9 |
| NDK | | X4 | >20 | >20 |
| | S613A | | >20 | >20 |
| | W614A | | 6.3 | 18.9 |
| JR-CSF | | R5 | >20 | >20 |
| | S613A | | >20 | >20 |
| | W614A | | 8.1 | 19.5 |
| YU-2 | | R5 | >20 | >20 |
| | S613A | | >20 | >20 |
| | W614A | | 10.3 | 20 |
| ROD | | HIV-2 | | |
| | S613A | | >20 | >20 |
| | W614A | | >20 | >20 |

TABLE 3

Characteristics of and neutralizing activity of HIV-infected patients producing anti-W614A-3S/gp41 Ab specifics for the W614A 3S/gp41 mutant.

| | HIV-infected patients | | | | | |
|---|---|---|---|---|---|---|
| | #105[a] | #24 | #44 | #65 | #71 | #109 |
| CD4 count/mm$^3$ | 752 | 825 | 816 | 650 | 856 | 1040 |
| CD4/CD8 ratio | 0.7 | 1.0 | 1.1 | 0.8 | 0.7 | 1.2 |
| Viral load | <20 | <20 | <20 | <20 | <20 | <20 |
| Anti-W614A Ab (AU/mL) | <10 | 220 | 220 | 140 | 150 | 250 |
| NAb activity in plasma[b] (IC$_{50}$/IC$_{95}$) | | | | | | |
| NL4.3 | <40/<40 | 1280/75 | 1115/56 | 827/<40 | 452/<40 | >2000/875 |
| YU-2 | <40/<40 | 480/<40 | 360 < 40 | 220/<40 | 128/<40 | 1120/65 |
| NAb activity with purified Ab[c] (IC$_{50}$/IC$_{95}$) | | | | | | |
| NL4.3 | >2/>2 | 0.3/1.5 | 0.3/1.6 | 1.5/>2 | 1.8/>2 | <0.2/0.6 |
| NDK | >2/>2 | 0.4/1.9 | 0.6/>2 | 1.8/>2 | 1.9/>2 | <0.2/0.9 |
| JRCSF | >2/>2 | 0.8/>2 | 0.9/>2 | >2/>2 | >2/>2 | 0.2/1.6 |

TABLE 3-continued

Characteristics of and neutralizing activity of HIV-infected patients producing anti-W614A-3S/gp41 Ab specifics for the W614A 3S/gp41 mutant.

| | HIV-infected patients | | | | | |
|---|---|---|---|---|---|---|
| | #105[a] | #24 | #44 | #65 | #71 | #109 |
| YU-2 | >2/>2 | 1.4/>2 | 1.3/>2 | 1.8/>2 | 1.9/>2 | 0.3/1.9 |
| ROD | >2/>2 | >2/>2 | >2/>2 | >2/>2 | >2/>2 | >2/>2 |
| NAb activity with purified Ab[d] ($IC_{50}/IC_{95}$) | | | | | | |
| NL4.3 | >2/>2 | 0.4/1.6 | 0.4/1.9 | 1.6/>2 | 1.9/>2 | <0.2/1.1 |
| BRU | >2/>2 | 0.5/>2 | 0.9/>2 | 1.9/>2 | >2/>2 | 0.3/2.6 |
| JRCSF | >2/>2 | 0.9/>2 | 1.4/>2 | >2/>2 | >2/>2 | 0.9/1.9 |
| YU-2 | >2/>2 | 1.7/>2 | 1.6/>2 | >2/>2 | >2/>2 | 0.6/1.7 |
| ROD | >2/>2 | >2/>2 | >2/>2 | >2/>2 | >2/>2 | >2/>2 |

[a]#107: HIV-infected sample, which do not produced anti-W614A-3S/gp Ab, but 125 AU/mL of anti-3S WT Ab. Specific Abs were immuno-purified from the sera with the 3S-WT peptide, as control.
[b]NAb activity in serum is expressed as the reciprocal dilution of heat-inactivated plasma that established 50% ($IC_{50}$) or 95% ($IC_{95}$) inhibition, respectively, of virus infection in Hela P4C5 cells.
[c] NAb activity in purified Ab is expressed in micrograms of Ab that established 50% ($IC_{50}$) or 95% ($IC_{95}$) inhibition, respectively, of virus infection in Hela P4C5 cells.
[d]NAb activity in purified Ab is expressed in micrograms of Ab that established 50% ($IC_{50}$) or 95% ($IC_{95}$) inhibition, respectively, of virus infection in TZM-bl cells.

TABLE 4

| | polypeptides | | | | | | |
|---|---|---|---|---|---|---|---|
| | WT | S613A | W614A | S615A | N616A | K617A | S618A |
| Adj | <1:20 | <1:20 | <1:20 | <1:20 | <1:20 | <1:20 | <1:20 |
| WT | >1:1280 | 1:1280 | <1:20 | 1:320 | 1:160 | 1:640 | 1:320 |
| M1 | 1:1280 | >1:1280 | 1:20 | 1:640 | 1:320 | 1:640 | 1:640 |
| M2 | 1:40 | 1:40 | >1:1280 | 1:20 | 1:80 | <1:20 | 1:20 |
| M3 | 1:320 | 1:320 | <1:20 | >1:1280 | 1:320 | 1:160 | 1:320 |
| M4 | 1:640 | 1:640 | <1:20 | 1:640 | >1:1280 | 1:80 | 1:160 |
| M5 | 1:1280 | 1:1280 | <1:20 | 1/80 | 1/40 | >1:1280 | 1:80 |
| M6 | 1:640 | 1:640 | 1:20 | 1:160 | 1:160 | 1:40 | >1:1280 |

The invention claimed is:

1. An antibody directed against an antigenic peptide of Formula I:

Nt-S-X1-X2-X3-K-X4-Ct (I) [Nt-SEQ ID No 1-Ct]   Formula I wherein

Nt comprises a peptide of from 0 to 50 amino acids in length,

Ct comprises a peptide of from 0 to 50 amino acids in length, and each of X1 to X4 is an amino acid residue, wherein:
(i) X1 is the specific amino acid W or (ii) X1 is any amino acid residue except W,
(i) X2 is the specific amino acid S or (ii) X2 is any amino acid residue except S,
(i) X3 is the specific amino acid N or (ii) X3 is any amino acid residue except N,
(i) X4 is the specific amino acid S or (ii) X4 is any amino acid residue except S, with the proviso that three out of the four amino acid residues X1, X2, X3 and X4 are an amino acid as defined in (i) above, and the remaining amino acid residue is any amino acid residue except the amino acid residue as defined in (i), and wherein the antigenic peptide is not the peptide of SEQ ID No 16.

2. The antibody according to claim 1, wherein the antigenic peptide of formula (I) is selected from the group consisting of:

Nt-S-X-S-N-K-S-Ct (Ia) - (Nt-SEQ ID No2-Ct),

Nt-S-W-X-N-K-S-Ct (Ib) - (Nt-SEQ ID No 3-Ct),

Nt-S-W-S-X-K-S-Ct (Ic) - (Nt-SEQ ID No 4-Ct), and

Nt-S-W-S-N-K-X-Ct (Id) - (Nt-SEQ ID No 5-Ct), wherein:

X is any amino acid residue except: W for (Ia), S for (Ib), N for (Ic) and S for (Id).

3. The antibody according to claim 2, wherein the antigenic peptide of formula (I) is selected from the group consisting of:

```
Nt-SASNKS-Ct (Nt-SEQ ID No 6-Ct),

Nt-SWANKS-Ct (Nt-SEQ ID No 7-Ct),

Nt-SWSAKS-Ct (Nt-SEQ ID No 8-Ct),
and

Nt-SWSNKA-Ct (Nt-SEQ ID No 9-Ct).
```

4. The antibody according to claim 1, wherein Nt is an amino acid sequence of 1 to 10 amino acid residues in length.

5. The antibody according to claim 1, wherein Nt comprises the amino acid sequence PWNA [SEQ ID No 10].

6. The antibody according to claim 1, wherein Ct is an amino acid sequence of 1 to 10 amino acid residues in length.

7. The antibody according to claim 1, wherein Ct comprises the amino acid sequence LDDIW [SEQ ID No 11].

8. The antibody according to claim 1, wherein meaning (ii) of each of X1, X2, X3 and X4 is selected from the group consisting of Alanine (Ala or A), Cysteine (Cys or C), Glycine (Gly or G), Proline (Pro or P) and Valine (Val or V).

9. The antibody according to claim 1, wherein the antigenic peptide is selected from the group consisting of:

```
PWNASASNKSLDDIW (SEQ ID No 12),

PWNASWANKSLDDIW (SEQ ID No 13),

PWNASWSAKSLDDIW (SEQ ID No 14),
and

PWNASWSNKALDDIW (SEQ ID No 15).
```

10. The antibody according to claim 1, wherein the antigenic peptide of formula (I) is covalently linked to a carrier molecule.

11. The antibody according to claim 1, wherein the antigenic peptide of formula (I) is combined with at least one adjuvant of immunity.

12. The antibody according to claim 1, wherein the said antibody is a broadly neutralizing anti-HIV-1 antibody.

13. A medicament for preventing and/or treating an HIV-1-infected individual comprising an antibody according to claim 1.

14. A method for preventing and/or treating an infection by the HIV-1 virus in an individual comprising the administration to the said individual of an antibody according to claim 1.

* * * * *

SEQUENCE LISTING

<160> NUMBER OF SEQ ID NOS: 20

<210> SEQ ID NO 1
<211> LENGTH: 6
<212> TYPE: PRT
<213> ORGANISM: artificial sequence
<220> FEATURE:
<223> OTHER INFORMATION: Synthetic peptide
<220> FEATURE:
<221> NAME/KEY: misc_feature
<222> LOCATION: (1)..(6)
<223> OTHER INFORMATION: Three out of the four amino acid residues
      located in positions 2, 3, 4 and 6 have their meaning (i) and the
      remaining fourth amino acid residue has its meaning (ii)
<220> FEATURE:
<221> NAME/KEY: misc_feature
<222> LOCATION: (2)..(2)
<223> OTHER INFORMATION: means (i) W or (ii) means any of A, R, D, N, C,
      Q, E, G, H, I, L, K, F, M, P, S, T, Y, or V
<220> FEATURE:
<221> NAME/KEY: misc_feature
<222> LOCATION: (3)..(3)
<223> OTHER INFORMATION: (i) means S or (ii) means any of A, R, N, D, C,
      Q, E, G, H, I, L, F, M, P, K, T, Y, W or V
<220> FEATURE:
<221> NAME/KEY: misc_feature
<222> LOCATION: (4)..(4)
<223> OTHER INFORMATION: (i) means N or (ii) means any of A, R, S, D, C,
      Q, E, G, H, I, K, L, F, M, P, T, Y, W or V
<220> FEATURE:

```
<221> NAME/KEY: misc_feature
<222> LOCATION: (6)..(6)
<223> OTHER INFORMATION: (i) means S or (ii) means any of A, R, N, D, C,
      Q, E, G, H, I, K, L, F, M, P, T, Y, W or V

<400> SEQUENCE: 1

Ser Xaa Xaa Xaa Lys Xaa
1               5

<210

```
Ser Trp Ser Asn Lys Xaa
1               5

<210> SEQ ID NO 6
<211> LENGTH: 6
<212> TYPE: PRT
<213> ORGANISM: artificial sequence
<220> FEATURE:
<223> OTHER INFORMATION: Synthetic peptide

<400> SEQUENCE: 6

Ser Ala Ser Asn Lys Ser
1               5

<210> SEQ ID NO 7
<211> LENGTH: 6
<212> TYPE: PRT
<213> ORGANISM: artificial sequence
<220> FEATURE:
<223> OTHER INFORMATION: Synthetic peptide

<400> SEQUENCE: 7

Ser Trp Ala Asn Lys Ser
1               5

<210> SEQ ID NO 8
<211> LENGTH: 6
<212> TYPE: PRT
<213> ORGANISM: artificial sequence
<220> FEATURE:
<223> OTHER INFORMATION: Synthetic peptide

<400> SEQUENCE: 8

Ser Trp Ser Ala Lys Ser
1               5

<210> SEQ ID NO 9
<211> LENGTH: 6
<212> TYPE: PRT
<213> ORGANISM: artificial sequence
<220> FEATURE:
<223> OTHER INFORMATION: Synthetic peptide

<400> SEQUENCE: 9

Ser Trp Ser Asn Lys Ala
1               5

<210> SEQ ID NO 10
<211> LENGTH: 4
<212> TYPE: PRT
<213> ORGANISM: artificial sequence
<220> FEATURE:
<223> OTHER INFORMATION: Synthetic peptide

<400> SEQUENCE: 10

Pro Trp Asn Ala
1

<210> SEQ ID NO 11
<211> LENGTH: 5
<212> TYPE: PRT
<213> ORGANISM: artificial sequence
<220> FEATURE:
<223> OTHER INFORMATION: Synthetic peptide

<400> SEQUENCE: 11

Leu Asp Asp Ile Trp
```

-continued 1               5

<210> SEQ ID NO 12
<211> LENGTH: 15
<212> TYPE: PRT
<213> ORGANISM: artificial sequence
<220> FEATURE:
<223> OTHER INFORMATION: Synthetic peptide

<400> SEQUENCE: 12

Pro Trp Asn Ala Ser Ala Ser Asn Lys Ser Leu Asp Asp Ile Trp
1               5                   10                  15

<210> SEQ ID NO 13
<211> LENGTH: 15
<212> TYPE: PRT
<213> ORGANISM: artificial sequence
<220> FEATURE:
<223> OTHER INFORMATION: Synthetic peptide

<400> SEQUENCE: 13

Pro Trp Asn Ala Ser Trp Ala Asn Lys Ser Leu Asp Asp Ile Trp
1               5                   10                  15

<210> SEQ ID NO 14
<211> LENGTH: 15
<212> TYPE: PRT
<213> ORGANISM: artificial sequence
<220> FEATURE:
<223> OTHER INFORMATION: Synthetic peptide

<400> SEQUENCE: 14

Pro Trp Asn Ala Ser Trp Ser Ala Lys Ser Leu Asp Asp Ile Trp
1               5                   10                  15

<210> SEQ ID NO 15
<211> LENGTH: 15
<212> TYPE: PRT
<213> ORGANISM: artificial sequence
<220> FEATURE:
<223> OTHER INFORMATION: Synthetic peptide

<400> SEQUENCE: 15

Pro Trp Asn Ala Ser Trp Ser Asn Lys Ala Leu Asp Asp Ile Trp
1               5                   10                  15

<210> SEQ ID NO 16
<211> LENGTH: 30
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: ACETYLATION

<400> SEQUENCE: 16

Asn His Asn His Arg Ile Arg Thr Asn Pro Ala Ile Val Lys Thr Glu
1               5                   10                  15

Asn Ser Trp Ser Asn Lys Ala Lys Ser Ile Cys Gln Gln Gln
                20                  25                  30

<210> SEQ ID NO 17
<211> LENGTH: 6

```
<212> TYPE: PRT
<213> ORGANISM: artificial sequence
<220> FEATURE:
<223> OTHER INFORMATION: Synthetic poly-histidine tag

<400> SEQUENCE: 17

His His His His His His
1               5

<210> SEQ ID NO 18
<211> LENGTH: 16
<212> TYPE: PRT
<213> ORGANISM: artificial sequence
<220> FEATURE:
<223> OTHER INFORMATION: Synthetic HIV-1 HXB2 strain-derived gp41
      peptide

<400> SEQUENCE: 18

Cys Pro Trp Asn Ala Ser Trp Ser Asn Lys Ser Leu Asp Asp Ile Trp
1               5                   10                  15

<210> SEQ ID NO 19
<211> LENGTH: 16
<212> TYPE: PRT
<213> ORGANISM: artificial sequence
<220> FEATURE:
<223> OTHER INFORMATION: Synthetic S613A mutated peptide

<400> SEQUENCE: 19

Cys Pro Trp Asn Ala Ala Trp Ser Asn Lys Ser Leu Asp Asp Ile Trp
1               5                   10                  15

<210> SEQ ID NO 20
<211> LENGTH: 16
<212> TYPE: PRT
<213> ORGANISM: artificial sequence
<220> FEATURE:
<223> OTHER INFORMATION: Synthetic K617A mutated peptide

<400> SEQUENCE: 20

Cys Pro Trp Asn Ala Ser Trp Ser Asn Ala Ser Leu Asp Asp Ile Trp
1               5                   10                  15
```